(12) United States Patent  
Isaacson et al.

(10) Patent No.: US 7,169,145 B2  
(45) Date of Patent: Jan. 30, 2007

(54) TUNED RETURN ELECTRODE WITH MATCHING INDUCTOR

(75) Inventors: James D. Isaacson, Salt Lake City, UT (US); Paul R. Borgmeier, Salt Lake City, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 220 days.

(21) Appl. No.: 10/719,333

(22) Filed: Nov. 21, 2003

(65) Prior Publication Data

US 2005/0113817 A1    May 26, 2005

(51) Int. Cl.  
*A61B 18/04* (2006.01)

(52) U.S. Cl. .......................................... 606/35; 606/34
(58) Field of Classification Search ............ 606/26–31, 606/34, 35, 41, 42; 607/101–102  
See application file for complete search history.

(56) References Cited

U.S. PATENT DOCUMENTS

| | | | |
|---|---|---|---|
| 3,089,496 A | 5/1963 | Degelman | 128/303.14 |
| 3,543,760 A | 12/1970 | Bolduc | 128/416 |
| 3,601,126 A * | 8/1971 | Estes | 606/35 |
| 3,720,209 A | 3/1973 | Bolduc | 128/2.06 E |
| 3,848,600 A | 11/1974 | Patrick, Jr. et al. | 128/303.13 |
| 4,088,133 A | 5/1978 | Twentier | 128/303.13 |
| 4,092,985 A | 6/1978 | Kaufman | 128/303.13 |
| 4,094,320 A | 6/1978 | Newton et al. | 128/303.14 |
| 4,117,846 A | 10/1978 | Williams | 128/303.13 |
| 4,166,465 A | 9/1979 | Esty et al. | 128/303.13 |
| 4,188,927 A | 2/1980 | Harris | |
| 4,200,104 A | 4/1980 | Harris | 128/303.14 |
| 4,207,904 A | 6/1980 | Greene | 128/798 |
| 4,226,247 A | 10/1980 | Hauser et al. | 128/641 |
| 4,231,372 A | 11/1980 | Newton | 128/303.14 |
| 4,237,886 A | 12/1980 | Sakurada et al. | 128/303.13 |

(Continued)

FOREIGN PATENT DOCUMENTS

GB         1 480 736         7/1977

(Continued)

OTHER PUBLICATIONS

Wald, et al., "Accidental Burns Associated With Electrocautery," *JAMA*, Aug. 16, 1971, vol. 217, No. 7, pp. 916-921.

*Primary Examiner*—Roy D. Gibson  
(74) *Attorney, Agent, or Firm*—Workman Nydegger

(57) ABSTRACT

An electrosurgical return electrode for use in electrosurgery. The return electrode is self-limiting and self-regulating as to maximum current and temperature rise to prevent patient trauma. An inductor is coupled in series with the return electrode. The inductor counteracts at least a portion of the impedance of the return electrode and the patient to optimize the flow of the current when the amount of contact area between the patient and the return electrode is sufficient to perform electrosurgery. The inductor may also be variable to allow the overall impedance of the electrosurgical circuit to be adjusted and tuned to work properly and safely with a particular patient and the other equipment used to perform electrosurgery. A conductor member operates with circuitry that indicates to a user when the contact area between the patient and the self-limiting member and/or return electrode is below a given threshold.

69 Claims, 13 Drawing Sheets

U.S. PATENT DOCUMENTS

| | | | |
|---|---|---|---|
| 4,237,887 A | 12/1980 | Gonser | 128/303.14 |
| 4,267,840 A | 5/1981 | Lazar et al. | 128/303.13 |
| 4,304,235 A | 12/1981 | Kaufman | 128/303.13 |
| 4,384,582 A | 5/1983 | Watt | 128/303.13 |
| 4,387,714 A | 6/1983 | Geddes et al. | 128/303.13 |
| 4,669,468 A | 6/1987 | Cartmell et al. | 128/303.13 |
| 4,770,173 A | 9/1988 | Feucht et al. | 128/303.13 |
| 4,799,480 A | 1/1989 | Abraham et al. | 128/303.13 |
| 5,352,315 A | 10/1994 | Carrier et al. | 156/267 |
| 5,354,790 A | 10/1994 | Keusch et al. | 523/300 |
| 5,520,683 A | 5/1996 | Subramaniam et al. | 606/32 |
| 5,830,212 A | 11/1998 | Cartmell et al. | |
| 5,836,942 A | 11/1998 | Netherly et al. | 606/32 |
| 6,053,910 A | 4/2000 | Fleenor | 606/32 |
| 6,083,221 A | 7/2000 | Fleenor et al. | 606/32 |
| 6,454,764 B1 | 9/2002 | Fleenor et al. | 606/32 |
| 6,547,786 B1* | 4/2003 | Goble | 606/34 |
| 6,666,859 B1 | 12/2003 | Fleenor et al. | 606/32 |
| 2005/0101947 A1* | 5/2005 | Jarrard et al. | 606/35 |

FOREIGN PATENT DOCUMENTS

| | | |
|---|---|---|
| GB | 2 052 269 | 1/1981 |
| JP | S55-168317 | 5/1979 |
| JP | S57-154409 | 9/1982 |
| JP | S57-188250 | 11/1982 |
| JP | S63-54148 | 3/1988 |

* cited by examiner

TUNED RETURN ELECTRODE WITH
MATCHING INDUCTOR

BACKGROUND OF THE INVENTION

1. The Field of the Invention

The present invention relates generally to electrosurgical systems. More specifically, the present invention relates to electrosurgical return electrodes that are adapted for providing safe and effective electrosurgery.

2. The Relevant Technology

As is known to those skilled in the art, modern surgical techniques typically employ radio frequency (RF) power to cut tissue and coagulate bleeding encountered in performing surgical procedures. For historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical tool for both cutting and coagulating the tissue of a patient. Every monopolar electrosurgical generator system must have an active electrode that is applied by the surgeon to the patient at the surgical site and a return path from the patient back to an electrosurgical generator that provides the RF power used during electrosurgical procedures. The active electrode at the point of contact with the patient must be small to produce a high current density resulting in a surgical effect of cutting or coagulating tissue. The return electrode, which carries the same current as the active electrode, must be large enough in effective surface area at the point of communication with the patient so that the density of the electrosurgical current flowing from the patient to the return electrode is limited to safe levels. If the density of the electrosurgical current is relatively high at the return electrode, the temperature of the patient's skin and tissue will rise in this area and can result in an undesirable patient burn.

In 1985, the Emergency Care Research Institute, a well-known medical testing agency, published the results of testing it had conducted on electrosurgical return electrode site burns, stating that the heating of body tissue to the threshold of necrosis occurs when the current density exceeds 100 milliamperes per square centimeter. The Association for the Advancement of Medical Instrumentation ("AAMI") has published standards that require that the maximum patient surface tissue temperature adjacent an electrosurgical return electrode should not rise more than six degrees (6°) Celsius under stated test conditions.

Over the past twenty years, products have been developed in response to the medical need for a safer return electrode. One advancement in return electrode technology was the development of a flexible electrode to replace the small, about 12×7 inches, flat stainless steel plate electrode typically in use during electrosurgical procedures. This plate electrode was typically coated with a conductive gel, placed under the patient's buttocks, thigh, shoulders, or any other location, and relied upon gravity to ensure adequate contact area. These flexible electrodes, which are generally about the same size as the stainless steel plates, are coated with a conductive or dielectric polymer and have an adhesive border on them so they will remain attached to the patient without the aid of gravity. By the early 1980's, most hospitals in the United States were using flexible electrodes. Flexible electrodes resulted in fewer patient return electrode burns but resulted in additional surgical costs in the United States of several tens of millions of dollars each year because each electrode had to be disposed of after use. Even with this improvement, hospitals were still experiencing some patient burns caused by electrodes that would accidentally fall off or partially separate from the patient during surgery.

In an attempt to minimize the potential for patient burns, contact quality monitoring systems were developed. Contact quality monitoring systems are adapted to monitor the contact area of an electrode that is in contact with a patient and turn off the electrosurgical generator whenever there is insufficient contact area between the patient and the electrode. Such circuits are shown, for example, in U.S. Pat. No. 4,200,104 issued to Harris, and entitled "Contact Area Measurement Apparatus for Use in Electrosurgery" and; U.S. Pat. No. 4,231,372, issued to Newton, and entitled "Safety Monitoring Circuit for Electrosurgical Unit," the disclosures of which are incorporated by this reference. Contact quality monitoring systems have resulted in additional reduction in patient return electrode burns, but require special disposable electrodes, resulting in an increase in the cost per procedure. Twenty years after these systems were first introduced, only 75 percent of all the surgical operations performed in the United States use contact quality monitoring systems because of the increased costs and other factors.

Self-limiting electrosurgical return electrodes provide an alternative to contact quality monitoring systems. Self-limiting electrosurgical return electrodes allow electrosurgery to be performed when the contact area between the patient and the pad is sufficient to limit the density of the electrosurgical current to safe levels and when there are not too many materials placed between the patient and the pad. When the contact area between the patient and the return electrode falls below a minimum contact area or when too many materials are placed between the patient and the pad, the properties of the pad limit the flow of current to prevent a patient burn.

While self-limiting electrodes are typically reusable and provide current limiting, the impedance properties of the pad can result in unnecessary limiting of the electrosurgical current even where the contact area is sufficient to prevent patient burns. For example, during surgeries that require high current flow such as trans-urethral resection of the prostate procedures (TURP), though the contact area may be sufficient to conduct safe electrosurgery, small increases in impedance can noticeably affect the current flow. Additionally, procedures involving small pediatric patients can result in diminished current flow due to the relatively small contact area of the patient with the pad and the resulting increases in impedance. This is particularly true for neonatal patients, where the small size and mass of the patients have rendered present applications impractical.

BRIEF SUMMARY OF THE INVENTION

The present invention is directed to an electrosurgical return electrode adapted to prevent patient burns. The return electrode provides a bulk impedance that provides self-limiting properties to the electrode. The bulk impedance of the electrosurgical return electrode allows the return electrode to be self-limiting and can result from the properties of the semi-insulating member, the conductor member, a combination of both the semi-insulating member and the conductor member, or a combination of two or more of the semi-insulating member, the conductor, clothing of the patient, blankets, sheets, and other materials that are disposed between the patient and the return electrode.

According to one illustrative embodiment of the present invention, an inductor is coupled in series with a capacitive electrosurgical return electrode. Inclusion of the inductor optimizes the flow of the electrosurgical current by minimizing the effective impedance of the electrosurgical return electrode when the amount of contact area between the patient and the electrosurgical return electrode is sufficient to conduct electrosurgery or where materials are placed between the patient and the electrosurgical return electrode.

According to another illustrative embodiment of the present invention, a capacitor is coupled in series with an inductive electrosurgical return electrode. Including the capacitor optimizes the flow of the electrosurgical current by minimizing the effective impedance of the electrosurgical return electrode when the amount of contact area between the patient and the electrosurgical return electrode is sufficient to conduct electrosurgery.

According to another illustrative embodiment of the present invention, the electrosurgical return electrode has a bulk impedance sufficient to prevent a patient burn when the contact area between the patient and the electrode is below a given threshold. The conductor member is adapted for use with circuitry that indicates to a user when the contact area between the patient and the self-limiting member and/or return electrode is below a given threshold.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

An electrosurgical return electrode is provided having a bulk impedance sufficient to prevent a patient burn when the contact area between the patient and the electrode is below a given threshold. According to one aspect of the invention, an inductor is coupled in series with a capacitor as part of an electrosurgical circuit. In the embodiment, an electrosurgical return electrode can include a capacitive electrosurgical return electrode that is utilized with a series inductor. Alternatively, the electrosurgical return electrode can include an inductive electrosurgical return electrode that is utilized with a series capacitor. Where a series inductor is utilized, the inductor optimizes the flow of the electrosurgical current by counteracting the capacitive impedance of the electrosurgical return electrode when the amount of contact area between the patient and the electrosurgical return electrode is sufficient to prevent patient burns. The conductor member, such as a split plate, may be adapted for use with circuitry that indicates to a user when the contact area between the patient and the return electrode is below a given threshold.

Series Inductor

The following discussion will be directed to a capacitive electrosurgical return electrode utilized with a series inductor to minimize the effective impedance of the electrosurgical return electrode. While a complete discussion of the series capacitor for use with an inductive electrosurgical return electrode is not included, as will be appreciated by those skilled in the art, the principles discussed with reference to the series inductor employed with a capacitive electrosurgical return electrode can be utilized to minimize the bulk impedance of an inductive electrosurgical return electrode with a series capacitor.

Figure 1:
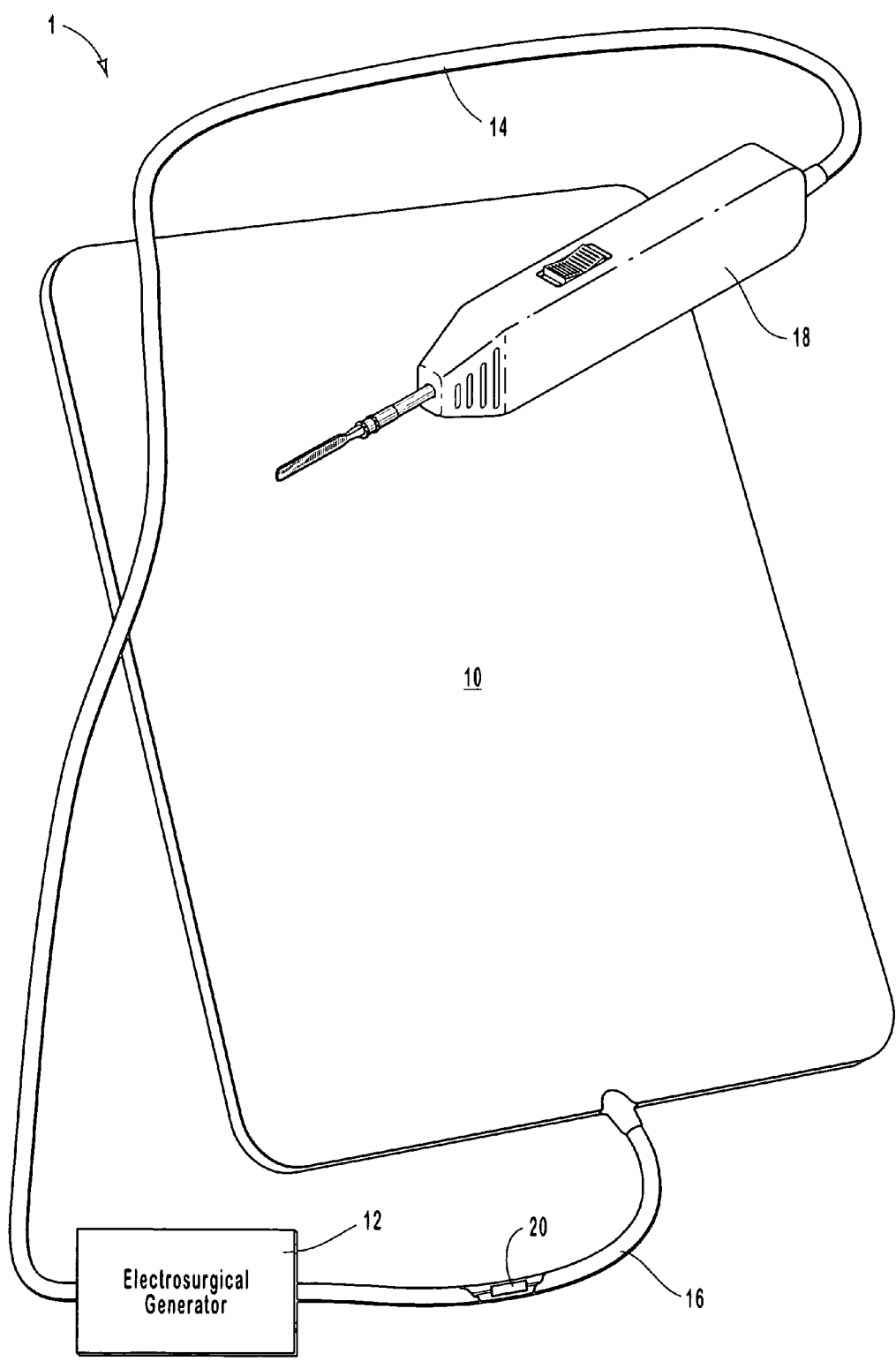
FIG. 1 is a perspective view of an electrosurgical system illustrating an inductor connected in series with an electrosurgical return electrode.

With reference now to FIG. 1, there is shown an electrosurgical system 1 having an inductor coupled in series with a return electrode. This inductor minimizes the impedance in an electrosurgical circuit by counteracting all or a portion of the capacitive reactance resulting from the bulk impedance. System 1 includes a return electrode 10, an electrosurgical generator 12, and an inductor 20. There are also shown conductor members 14 and 16 that electrically connect return electrode to an electrosurgical tool 18 and electrosurgical generator 12 respectively. Electrosurgical generator 12 generates an electrosurgical current, i.e. radio frequency (RF) energy, which is conveyed to electrosurgical tool 18 by way of conductor member 14.

Electrosurgical tool 18 utilizes the electrosurgical current during a procedure to cut and coagulate tissue of a patient resting on return electrode 10. Various types of electrosurgical generators 12 are known to those skilled in the art in light of the teaching contained herein. The electrosurgical current is returned to electrosurgical generator 12 through the patient and return electrode 10 by utilizing conductor member 16 as the return path. In the illustrated embodiment, conductor members 14 and 16 comprise cabling that operate as conductors of the electrosurgical current. These conductor members 14 and 16 are illustrative of exemplary structure capable of performing the function of means for conveying RF energy from one component to another component. One skilled in the art would identify various other structures capable of performing the desired function.

Return electrode 10 is adapted to limit the density of electrosurgical current flowing from a patient resting on return electrode 10 back to the electrosurgical generator. Return electrode 10 is adapted to provide self-limiting properties to prevent patient burns. The self-limiting properties of return electrode 10 increase the effective impedance of return electrode 10 as the contact area between the patient and return electrode 10 decreases to limit the flow of electrosurgical current. By limiting the flow of electrosurgical current, use of electrosurgical tool 18 is inhibited and the possibility of patient burns is minimized. Illustrative materials and geometries for return electrode 10 are described in U.S. Pat. No. 6,454,764 entitled "Self-Limiting Electrosurgical Return Electrode" and other related patent applications, the disclosures of which is incorporated herein by reference.

The self-limiting aspects of the electrosurgical return electrode are the result of the impedance properties of the return electrode whether the impedance results from capacitive, resistive or inductive components or reactances. One impedance property of the return electrode is capacitive reactance resulting from the arrangement of the patient on return electrode 10. In one configuration, a parallel plate capacitor formed between the patient and the return electrode provides the capacitive reactance. The patient comprises one of the plates of the parallel plate capacitor and return electrode 10 comprises the opposing plate. Other elements such as bedding, coatings on return electrode 10, the patient's skin characteristics etc. form a gap and/or dielectric barrier between the opposing plates. The amount of capacitive reactance provided is dependent upon the amount of patient contact with return electrode 10, the proximity of the patient to return electrode 10 in non-contacting areas, the type and amount of bedding positioned between the patient and return electrode 10, the type and amount of coatings on return electrode 10, the characteristics of the patients body make-up, and a myriad of other factors.

While capacitive reactance provides a portion of the overall impedance needed to achieve the self-limiting features of the electrode, it can limit the flow of electrosurgical current at the electrosurgical interface when there is sufficient contact between the patient and the return electrode to prevent patient burns. The resulting diminished current flow is typically small and inconsequential during most surgical procedures. However, for some procedures where patient contact area is minimal (e.g. neonatal procedures) or unusually high current flow is needed (e.g. TURPS procedures) any diminished capacity can be important.

To maximize power transfer while maintaining the self limiting aspects of the electrode, the aggregate of the reactive impedances exhibited by the circuit (i.e. capacitance and inductance) should be minimized when the contact area between the patient and the electrode are sufficient to prevent patient burns. In other words, by creating an overall circuit that appears to be as resistive as possible, maximum power can be delivered by the circuit. Those skilled in the art recognize this concept as one of maximizing the amount of real power delivered to a circuit with respect to the amount of imaginary or reactive power existing in a circuit. One method of counteracting capacitive reactance in a circuit is by introducing into the circuit an appropriately constructed inductor, such as inductor 20.

Inductor 20 is connected in series with electrosurgical electrode 10. Inductor 20 is configured to minimize the effective impedance of the electrosurgical circuit when the amount of contact area between the patient and the electrosurgical return electrode is sufficient to conduct electrosurgery. Inductor 20 minimizes the effective impedance of the electrosurgical return electrode by counteracting the capacitive reactance. It is desirable that the power generated by the electrosurgical generator 12 be concentrated in the region where the surgeon's implement contacts the patient's tissue at the electrosurgical interface. Increasing the current flow in the electrosurgical circuit by reducing impedances other than at the electrosurgical interface allows for such a result.

Illustratively, Ohms law teaches that the relationship between Voltage (V), current (I), and impedance (Z) is given by:

$$I = \frac{V}{Z} \qquad (1)$$

If Voltage in the electrosurgical circuit is held constant, reducing the value of the aggregate impedance of the circuit causes a resultant increase in the current through circuit. The real power (P) dissipated at any component within the circuit is given by the equation:

$$P = I^2 R \qquad (2)$$

Applying this equation to the resistive impedance at the surgical interface, when the resistance (R) at the surgical interface remains constant, increasing the current (I) flow through the constant resistance increases the power dissipated by that resistance by a factor of the current squared. Thus, increasing the current flow in the circuit can be accomplished by reducing various impedances in the circuit. By increasing the current flow in the circuit, more of the available power is concentrated at the surgical interface.

The effective impedance of the electrosurgical return electrode 10 may significantly limit the amount of power delivered to the electrosurgical interface by reducing the overall current in the circuit. The impedance of the electrosurgical return electrode can be the sum of one or any combination of a resistive component, a capacitive component, and an inductive component. Inductor 20 is capable of reducing the magnitude of the effective impedance of the electrosurgical circuit by counteracting the capacitive component of the effective impedance of the electrosurgical return electrode 10. Reducing the magnitude of the effective impedance of the electrosurgical circuit results in increased flow of electrosurgical current and a resultant increase in power delivered by the electrosurgical current to the electrosurgical interface.

A variety of different types and configurations of inductors can be utilized in light of the present invention including, but not limited to, a solid state inductor or a mechanically tunable inductor. Further, various configurations of inductors may be used such as fixed value inductors or tunable inductors. Tunable inductors may be accomplished in several ways, including but not limited to, mechanically tunable inductors, inductor banks using mechanical or solid state switching to add and remove inductive elements, solid state inductors and digital power shaping circuits that generate electrical signals of appropriate phase and magnitude to counteract capacitive impedance elements. In the illustrated embodiment inductor 20 is coupled to conductor member 16. As will be appreciated by those skilled in the art, inductor 20 can be placed in a variety of positions within the system and in a variety of configurations without departing from the scope and spirit of the present invention. For example, the inductor can be placed in conductor member 14, electrosurgical tool 18, or electrosurgical generator 12. Further, one or more inductors may be used in system 1 to reduce the magnitude of the effective impedance.

Figure 2:
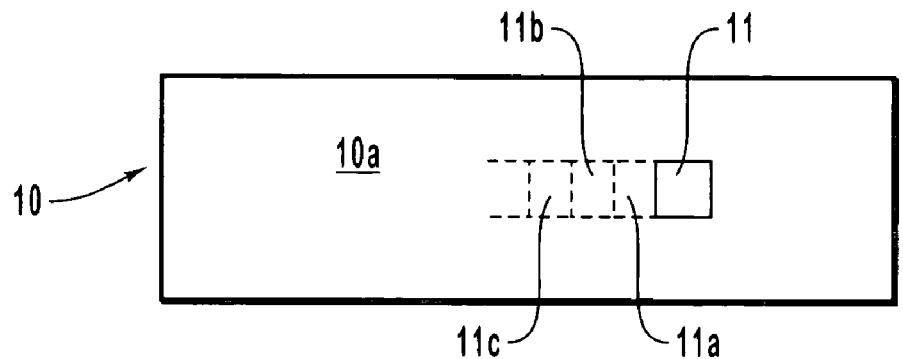
FIG. 2 is a top view of a return electrode illustrating the principles by which impedance varies as a function of contact area.

Now turning to FIG. 2, there will be seen a schematic representation of the top view of a return electrode 10 illustrating the self-limiting principles of return electrode 10. The effective impedance of return electrode 10 and its relationship to self-limiting principles illustrates the manner in which an inductor can be utilized to minimize the effective impedance of the electrosurgical return electrode. For instructional purposes of this description and to aid in the mathematical modeling of electrode 10, electrode 10 may be thought of as including a plurality of uniformly sized, continuous regions or segments as represented by regions 11a, 11b, 11c . . . 11n. One skilled in the art will appreciate, however, that electrode 10 may include discontinuous regions or segments.

It is known that, in contrast with the series circuit, combined resistive, inductive, and capacitive reactances, when connected in parallel, present a total effective impedance that is given by the formula:

$$z_{\textit{eff}} = \frac{1}{\frac{1}{z_1}+\frac{1}{z_2}+\frac{1}{z_3}+\frac{1}{z_4}+\frac{1}{z_5}+\frac{1}{z_6}} \quad (3)$$

Using an exemplary resistive circuit for ease of explanation, if 100 similar impedances, each of 100 ohms, were connected in parallel, the effective impedance $Z_{\textit{eff}}$ would equal one ohm. If half of such impedances were effectively disconnected, the remaining effective impedance would be two ohms, and if only one of the impedances were active in the circuit, the remaining effective impedance would be 100 ohms. Using these principles, the total effective impedance of electrode 10 can be rendered self-limiting due to properties of capacitors, resistors, and inductors in parallel.

Discrete segments of a resistive electrode formed from a uniform material function as resistors in parallel with the number of resistors in parallel corresponding with the number of discrete segments contributing to the effective impedance. Each discrete segment correlates with a portion of the surface area of the uniform material. In other words, the impedance of a resistor is, among other things, a function of the surface area of the face of the resistor. This relationship is described by the equation:

$$R = \rho\left(\frac{L}{A}\right) \quad (4)$$

In the equation R represents resistance, p represents a material constant, L represents the length of the resistor, and A represents the surface area. Increasing the surface area has the same effect as adding resistive components in parallel with one another. For example, doubling the surface area of the resistor has the effect of reducing the overall resistance by ½, the same as if two identically sized resistors were connected in parallel. A similar analysis can be performed for capacitive and inductive elements. As such, electrode 10 can be modeled as a plurality of distinct segments each capable of being added in a parallel configuration with each of the other segments of electrode 10.

Each of the segments of electrode 10 corresponding to segments 11a . . . 11n inherently has the capability of presenting an impedance. However, the number of such segments that are effectively active in parallel within the circuit is a direct function of the surface area of the patient that overlies the electrode. Thus, in the case of a large supine patient whose body is in effective contact with 50 percent (50%) of the upper surface of electrode 10, 50 percent of the segments corresponding to segments 11a–11n will be effectively in parallel in the circuit to form a given impedance. Where electrode 10 contains 100 segments of 1000 ohms each, the effective impedance operatively presented by the effective 50 percent of the electrode elements would be 20 ohms. Because 20 ohms is very small compared with the impedance at the surgical interface, a low percentage of the available energy is dissipated at the region of contact between the patient and electrode 10, and due also to the relatively large effective working area of electrode 10, current density, and temperature elevation are maintained below the danger thresholds mentioned above. When the impedance created by placing a patient on the electrode includes reactive impedances, such as capacitive and inductive impedances, even less of the energy available is dissipated at the region of contact between the patient and electrode 10 because reactive impedances do not dissipate real power.

Now, if for any reason, the effective contact area between the patient and electrode 10 were to be reduced to the surface of only one of segments 11a–11n, then the effective impedance would increase to 1000 ohms. As the contact area decreases, a point is reached in which the effective impedance rises to a level such that it diminishes the electrosurgical effect of tool or instrument 18 or otherwise prevents effective use of tool or instrument 18 by the surgeon. This diminishing of electrosurgical effect or effectiveness of tool or instrument 18 signals to the surgeon that the patient should be repositioned so as to present a greater surface area in contact with return electrode 10. As the effective impedance rises, the total circuit impedance would be increased so that the total current flow would be reduced to a value below that which would cause undesired trauma to the patient if the surgeon attempted to employ tool or instrument 18 without repositioning the patient.

When the effective contact area is large, the effective impedance is low such that the current at the surgeon's implement is high. Also, because the contact area is large and the total current flow is distributed across the entire contact area, the corresponding current density across return electrode 10 is low. This is the condition desired for performing surgery. However, as the effective surface area decreases, the impedance of return electrode 10 increases such that in electrosurgical generators that maintain a constant voltage, a corresponding decrease in the current at tool or instrument 18 (FIG. 1) results. When the effective surface area declines to some point, there will remain insufficient current at tool or instrument 18 to effectively conduct surgery. The point where effective surgery can no longer be conducted depends on many of the factors discussed herein including among other things the design of the electrosurgical generator, the design of electrode 10 and the materials placed between the patient and electrode 10. The parameters selected for the materials and dimensions of electrode 10 are chosen so that current density and corresponding tissue temperature elevation adjacent return electrode 10 does not exceed the limits mentioned in the introduction hereof. For example, in one embodiment return electrode 10 has a bulk impedance of at least 4,000 Ω·cm so as to limit the current density to safe levels. To facilitate description of the principles underlying the invention, the foregoing is described in terms of impedances whose principal components are resistances and capacitive reactances. However, the principles of the invention are also applicable to other embodiments in which the impedances include any combination of resistive, capacitive and/or inductive impedances.

While the above example has been framed in the context of a fixed voltage electrosurgical generator, some generators are designed to maintain a constant power output. Thus, as the effective contact area between the patient and electrode 10 decreases thereby causing an increase in impedance in the electrosurgical circuit, constant power generators will increase the voltage to maintain a constant power output at the operating site. Nonetheless, electrode 10 can limit current density and tissue heating using these generators. Those skilled in the art understand that even constant power electrosurgical generators have a designed maximum voltage level, so there exists a point where the electrosurgical generator does not increase power or voltage, and the constant voltage example described above is applicable.

Even when no designed maximum voltage level exists, electrode 10 can provide current limiting and heat limiting properties. Those skilled in the art understand that there are inherent characteristics in any electrosurgical generator that limit the amount of power that can be delivered by the generator. Just one example is that of the power supply used to power the electrosurgical generator. Generally, the power supply will contain self protective circuitry to limit the amount of power that can be generated by the power supply. Further, most power supplies include wire wound transformers that inherently have saturation points where they are no longer able to deliver increasing amounts of power. Thus, at some point, for all practical purposes, every electrosurgical generator begins to behave like the constant voltage example described above so that the current and heat limiting electrode 10 can be implemented.

By providing a return electrode 10 having both the desired bulk impedance and a sufficient surface area, the electrosurgical current is distributed sufficiently such that the current density does not result in a patient burn. It has been found that with selected materials and geometries, the self-limiting principles hereof can be achieved in a return electrode as small as about seven square inches (or about 45 square centimeters) in working surface area, while the preferable range of exposed upper working surface area of return electrode 10 lies in the range of from about 11 to 1,500 square inches (or about 70 to 9,680 square centimeters).

Return electrode 10 need not be in direct physical contact with the patient. Having a working surface area of this size eliminates the need for direct physical attachment, either directly to the skin of the patient or through gels. A patient can be in electrical connection with return electrode 10 without requiring the use of adhesives or gels. This also allows return electrode 10 to be re-used thereby eliminating the need and cost of disposable split-plate electrodes that are commonly used. This reduces the cost for using contact quality monitoring techniques to verify that the patient is sufficiently in contact with a return electrode to prevent high current densities that result in patient burns.

Additionally, it can be understood that the self-limiting characteristics or capabilities of return electrode 10 can be achieved where return electrode 10 is substantially enclosed within a semi-insulating member. Additionally, the self-limiting characteristics or capabilities can be provided in part, from materials, members or elements disposed between return electrode 10 and a patient. For instance, such other materials, members, or elements can include but are not limited to, linens, drawsheets, clothing, blankets, or the like. Therefore, electrode 10 has an effective bulk impedance sufficient to prevent a patient burn when the contact area between the patient and electrode 10 is below a given threshold.

The electrode 10 according to the invention hereof may be made of conductive plastic, rubber, or other flexible material which, when employed in electrode 10 will result in an effective impedance presented by each square centimeter of working surface sufficient to limit the current density to safe levels. Silicone or butyl rubber has been found to be particularly attractive materials as they are flexible, as well as readily washable and sterilizable. Alternatively, a portion of return electrode 10 may be made of inherently relatively high resistance flexible material altered to provide the requisite conductivity. For example, a silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors. A more complete discussion of self-limiting characteristics can be found in U.S. Pat. No. 6,454,764 entitled "Self-Limiting Electrosurgical Return Electrode," which is incorporated herein by reference.

Figure 3:
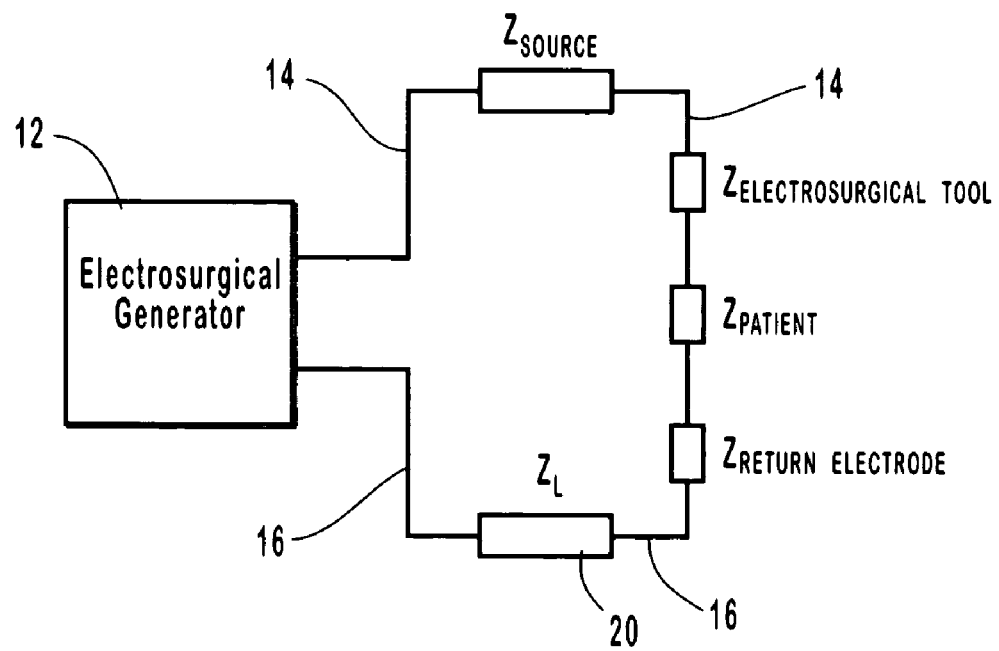
FIG. 3 is a schematic view illustrating the impedances presented to an electrosurgical generator and inductor coupled in series therewith.

With reference now to FIG. 3, there is shown a simplified electrical schematic diagram of an electrosurgical circuit illustrating the manner in which an inductor can be utilized to minimize the effective impedance of a return electrode. There are shown the typical impedances $z_{source}$, $z_{electrosurgical\ tool}$, $z_{patient}$, $z_{return\ electrode}$ effectively included in the operative path of an electrosurgical current during an operative procedure and an inductor 20 connected in series therewith. The inductor 20 is configured to minimize the effective impedance of the electrosurgical return electrode when the amount of contact area between the patient and the electrosurgical return electrode is safe with regard to current densities.

Electrosurgical generator 12 is adapted to provide an electrosurgical current. Electrosurgical generator 12 can be adapted to function as a constant current or voltage generator, a variable current or voltage generator, a constant power flow generator, a variable power flow generator or any other suitable type of generator. Electrosurgical generator 12 has an inherent impedance associated with it represented by $z_{source}$. Connected to electrosurgical generator 12 are conventional electrical conductor members 14 and 16 which respectively connect the generator 12 to the electrosurgical tool 18 represented by impedance $z_{electrosurgical\ tool}$ (where the impedance is largely a result of the configuration of the electrosurgical tool at the surgical interface) and a return electrode 10 represented by impedance $z_{return\ electrode}$. Impedance $z_{patient}$ is provided to represent the impedance presented by the patient's tissue lying between the operation site and the return electrode.

The diagram of FIG. 3 is a simplified version of the electrosurgical current circuit. The diagram generally considers circuit elements in terms of the principal impedances, including the impedances contributed by the surgical interface, the patient's body, and the return electrode, so as to clearly and succinctly illustrate principles of the invention, it should be understood that in reality certain other parameters would be encountered, parameters such as distributed inductance and distributed capacitance which, for purposes of clarity in illustration of the principles hereof, are likely relatively small and so are not considered in this description.

The initial embodiment, hereof, is that of an electrode operating in an exclusive capacitive mode or a combined resistive and capacitive mode. Accordingly, if the relatively small stray capacitive and inductive reactances are disregarded, the total effective impedance of the circuit will be equal to the sum of the individual impedances $z_{source}$, $z_{electrosurgical\ tool}$, $z_{patient}$, $z_{return\ electrode}$ and $z_L$ (the impedance of the inductor); and because essentially the same current will pass through all five, the voltage generated by electrosurgical generator 12 will be distributed across each impedance in the circuit in direct proportion to their respective values. The real power dissipated by each of the resistive elements of the circuit is dissipated in direct proportion to the value of the resistive element.

Because it is desirable that the power generated by the electrosurgical generator 12 be concentrated in the region where the surgeon's implement contacts the patient's tissue, i.e. the electrosurgical interface, it is desirable that the resistive component of the impedance represented by $z_{electrosurgical\ tool}$ be substantial and that current passing therethrough (and consequent power dissipation) be concentrated in a very small region. The latter is accomplished by making the region of contact with the patient at the operative site very small. By equation 4, resistance is inversely proportional to the area of the resistor. Thus as the area of the resistor, in this case the point of the electrosurgical tool 18, becomes smaller, the resistance of the electrosurgical tool becomes larger, with the resistance concentrated at the point of the electrosurgical tool. As such, the power dissipated directly at the surgical interface is increased with respect to the power dissipated at other locations in the circuit.

In contrast to the region where the surgeon's implement contacts the patient's tissue, it is desired that the effective impedance $Z_{return\ electrode}$ of the return electrode be minimized and that the current passing therethrough be distributed in a large region to avoid an undesirable patient burn. Accordingly, it is desired that the contact area between the patient and the return electrode 10 be maximized and the effective impedance of the return electrode be small. Return electrode 10 is rendered self-limiting to ensure that the current density of the current passing therethrough is limited so as not to result in a patient burn. As will be appreciated by those skilled in the art, a variety of combinations of resistive components, capacitive components, and/or inductive components can be utilized to achieve the self-limiting characteristics or capabilities of return electrode 10.

As previously discussed, inductor 20 is coupled in series with return electrode 10. Inductor 20 is configured to counteract the capacitive component of the effective impedance $z_{return\ electrode}$ of the electrosurgical return electrode. The impedance of the return electrode 10 can be presented by a resistive component, a capacitive component, and/or an inductive component, as shown by the following equations:

$$X_c = \frac{1}{j\omega C} \tag{5}$$

where $X_c$ is the capacitive reactance, $-j$ or $1/j$ is the vector direction of the capacitive reactance and is equal to $\sqrt{-1}$, $\omega$ is the frequency in Hertz of the electrosurgical current multiplied by $2\pi$, where $\pi$ is approximated to 3.14159, C is the capacitance in Farads;

$$X_L = j\omega L \tag{6}$$

Where $X_L$ is the inductive reactance, j is the vector direction of the inductive reactance and is equal to $\sqrt{-1}$, $\omega$ is the frequency in Hertz of the electrosurgical current multiplied by $2\pi$, and L is the inductance in Henrys (H). The total impedance of return electrode 10 is the sum of the resistive component, the capacitive component, and the inductive component and is given by the formula:

$$Z_{tot} = R + \frac{1}{j\omega C} + j\omega L \tag{7}$$

By noting that $j=-1/j$, it can be observed that a purely capacitive load is opposite in vector direction to a purely inductive load. By introducing an inductance into a capacitive circuit that is equal in magnitude to the capacitive impedance of the circuit, the capacitive impedance can be cancelled such that the phase angle between the voltage and current remains at zero resulting in a circuit that appears to be purely resistive. The relationship is demonstrated by the following equation.

$$Z_{tot} = R + \frac{1}{j}\left(\frac{1}{\omega C} - \omega L\right) \tag{8}$$

Equation 8 illustrates that, by substituting the vector direction $-1/j$ for the equivalent $-j$ for the inductive reactance, the vector direction can be factored out of the inductive and capacitive reactances. Once the vector direction is factored out, the magnitude of the inductive reactance is subtracted from the magnitude of the capacitive reactance. Thus, by selecting an appropriately sized inductive reactance, the effective capacitive reactance presented by the return electrode 10, can be minimized or eliminated. In other words, an inductive load can be utilized to minimize the capacitive reactance of the parallel plate capacitor when the amount of contact area between the patient and the electrosurgical return electrode is sufficient to limit the density of the electrosurgical current to safe levels.

Figure 4:
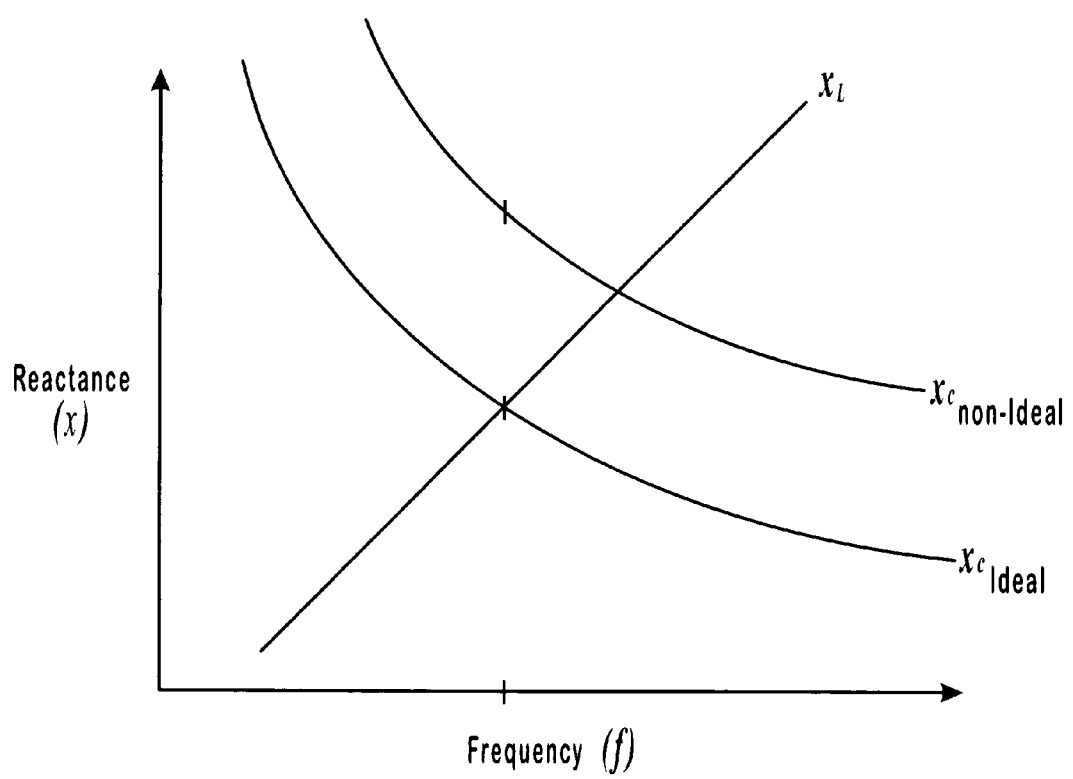
FIG. 4 is a chart illustrating in graphical form the relationship between capacitive reactance, inductive reactance, and frequency of an electrosurgical current.

With reference now to FIG. 4, there is shown the relationship between frequency of an electrosurgical current flowing through the return electrode and the reactance of a capacitor and an inductor. However, before proceeding to a consideration of such chart, it should be noted that the chart is simplified so as to illustrate the principles underlying the invention and does not represent actual data that may vary substantially. The graph illustrates that the magnitude of the inductive reactance and capacitive reactance vary according to the frequency of the electrosurgical current. The inductive reactance varies in proportion to the frequency of the electrosurgical current, while the capacitive reactance varies in inverse proportion to the frequency of the electrosurgical current. This is due to the fact that inductive reactance and capacitive reactance are determined using to represented by the equation:

$$\omega = 2\pi f \qquad (9)$$

where f is frequency in hertz (Hz).

Where the frequency of the electrosurgical current is constant, the amount of inductive reactance can be established by simply selecting an inductor 20 having a desired amount of inductance. Due to the fact that electrosurgical generators typically provide an electrosurgical current having a consistent frequency, the frequency is an ascertainable constant. Where the capacitance of the parallel plate capacitor and the frequency are also known, a selected inductive reactance can be utilized to minimize the orthogonal reactance of return electrode 10 relative to resistance. However, the capacitive reactance may be difficult to establish in some cases due to the fact that the self-limiting electrode is typically utilized such that the amount of contact area between the patient and the return electrode is in z variable. Additionally, the capacitive reactance can be affected by materials, such as linens, drawsheets, blankets, or other materials positioned between the patient and the electrosurgical return electrode. The relationship between contact area, interposed materials, and capacitive reactance is discussed in greater detail with reference to FIGS. 5A and 5B.

With continued reference to FIG. 4, in selecting a desired amount of inductive reactance, a user can determine an ideal capacitive reactance $X_{cIdeal}$ based on the desired contact area and properties of the materials between the patient and the electrosurgical return electrode. Once the amount of capacitive reactance for $X_{cIdeal}$ is determined for the frequency of the electrosurgical generator, an inductor can be selected that provides a desired amount of inductive reactance to counteract the capacitive reactance of $X_{cIdeal}$. The point of intersection of $X_{cIdeal}$ and $X_L$ indicates the frequency where the reactances of $X_{cIdeal}$ and $X_L$ counteract one another. As a result, where the actual capacitive reactance of the electrosurgical circuit is $X_{cIdeal}$, the series inductor will counteract the capacitive reactance and the overall impedance will be reduced by the magnitude of the capacitive reactance.

However, where the contact area and/or the materials between the patient and the electrosurgical return electrode vary from the desired contact area and/or the desired properties of the materials between the patient and the electrosurgical return electrode, the capacitive reactance will vary from $X_{cIdeal}$ as is shown with respect to $X_{cnon-ideal}$. Where the capacitive reactance is represented by $X_{cnon-ideal}$ rather than by $X_{cIdeal}$, the inductive reactance will continue to counteract the capacitive reactance presented by the electrosurgical circuit. However, the reduction in the overall impedance will not be reduced by the magnitude of the actual capacitive reactance of the circuit. Instead, the overall impedance of the electrosurgical circuit will be reduced by an inductive reactance provided by the inductor of the electrosurgical circuit. Where the capacitive reactance is greater than inductive reactance, as with $X_{cnon-ideal}$, a reduced net positive capacitive reactance will be produced. Where the capacitive reactance is less than the inductive reactance, a net inductive reactance will be produced.

While it may be desirable to completely eliminate the capacitive reactance, it may also be acceptable to simply reduce the amount of reactance in a circuit. For example, consider the case when the capacitive reactance of the large majority of patients undergoing surgery using the return electrode falls in a range between −50j Ohms and −800j Ohms. While a reactive impedance with a magnitude of 800 Ohms may not be acceptable, in some situations effective surgery may be performed so long as the magnitude of the reactive impedance is less than 400 Ohms. An inductor contributing an inductive reactance of 425j Ohms added in series with the circuit will cause the range of the reactances of the patients when combined with the inductive reactance of 425j Ohms to be between 375j Ohms to −375j Ohms. Because any value within this range is within the acceptable range requiring the magnitude of the reactance (either capacitive or inductive) to be less than 400 Ohms, an effective design can be implemented by simply adding a fixed value inductor in series with the return electrode.

As will be appreciated by those skilled in the art, a series capacitor can be utilized with a self-limiting electrosurgical return electrode having an inductive component without departing from the scope and spirit of the present invention. A series capacitor can be utilized relying on the principles describe with reference to FIG. 4. In the embodiment, the series capacitor provides a level of capacitive reactance needed to counteract the inductive reactance of the electrosurgical return electrode. A variety of types and configurations of series capacitors can be utilized without departing from the scope and spirit of the present invention.

Figure 5A:
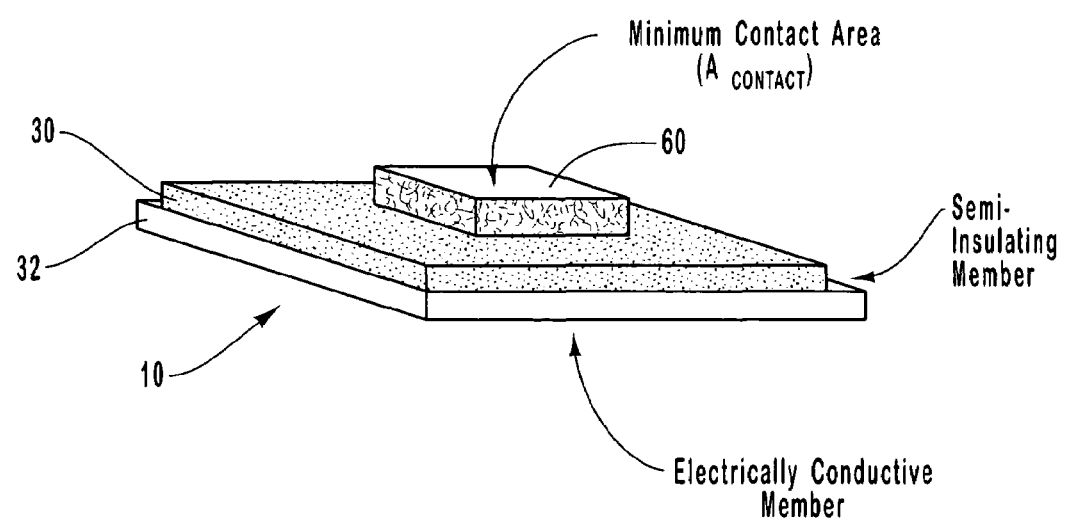
FIG. 5A is a perspective view illustrating a representative patient in contact with a semi-insulating member of a return electrode.

With reference now to FIG. 5A, there is shown a schematic representation of return electrode 10 and a patient in contact therewith. FIG. 5A is utilized to illustrate the relationship between the contact area and the capacitive reactance in order to describe how an inductor can be utilized to minimize the capacitive reactance of the return electrode while maintaining the self-limiting properties of the return electrode 10. There is shown a conducting layer 60 and a return electrode 10. In the illustrated embodiment, return electrode 10 comprises a semi-insulating member 30 and an electrically conductive member 32. Conducting layer 60 represents a patient resting on a semi-insulating member 30. Conducting layer 60 is configured to represent the minimum contact area required to limit the current density to safe levels.

As discussed with reference to FIG. 2, the number of such segments that are effectively active in parallel within the circuit is a direct function of the surface area of the patient that overlies return electrode 10. Where the surface area of the patient that overlies electrode 10 is at, or above, the minimum contact area, the total effective impedance is sufficiently low to permit the electrosurgical current to conduct safe and effective electrosurgery. Where the impedance is due primarily to a capacitive component and a resistive component, the amount of impedance is inversely proportional to the amount of patient contact area.

While the effective impedance is sufficiently low to conduct safe electrosurgery, under some conditions the effective impedance resulting from the contact area and the properties of the return electrode can result in current limiting of the electrosurgical current. This is often the result of a bulk impedance of a return electrode that exceeds 10,000 Ω·cm. For example, during surgeries that require high current flow such as trans-urethral resection of the prostate procedures (TURP), small increases in impedance can noticeably affect the current flow. Additionally, procedures involving small pediatric patients can result in diminished current flow due to the contact area of the patient with the pad and the resulting increases in impedance. This is particularly true for neonatal patients, where the small size and mass of the patients have rendered present applications impractical.

By placing inductor 20 (see FIG. 1) in series with return electrode 10, the magnitude of the effective impedance of the return electrode can be minimized. For example, during surgeries that require high current flow, inductor 20 can counteract the capacitive reactance component of the effective impedance of the return electrode. By counteracting the capacitive reactance, only the resistive component of the bulk impedance remains (assuming little or no inductive reactance in the return electrode.) Alternatively, an inductive reactance may be chosen to function with a range of capacitive reactances to limit the overall reactance below some given threshold. The capacitive reactance in the electrosurgical circuit is a function of several factors including the contact area of the patient to the return electrode. Where the majority of the effective impedance of the return electrode is due to capacitive reactance, an inductor providing a desired amount of inductance can be utilized to counteract all or a large part of the capacitive portion of the effective impedance of the return electrode thus reducing the overall magnitude of the effective impedance. By minimizing the magnitude of the effective impedance of the pad, surgeries that are sensitive to small changes in the effective impedance of the return electrode, such as pediatric, neonatal, and TURP procedures can be performed with minimal reduction in the current flow.

The capacitive reactance of the return electrode is determined in order to identify the amount of inductance to be provided by the inductor. As previously discussed, the capacitive reactance of a return electrode is defined by the equation:

$$X_c = \frac{1}{j\omega C} \tag{10}$$

While the frequency of a self-limiting return electrode can be controlled without difficulty, the amount of capacitance C can be more complicated to control.

A patient on a return electrode is somewhat similar in configuration to a parallel plate capacitor with the patient being one of the plates and the return electrode the other plate. Modeling the patient and return electrode as a parallel plate capacitor is not completely accurate, as edge effects and other stray capacitances may contribute to the overall capacitance. Nonetheless, a parallel plate capacitor model is instructive for illustrating various properties of certain embodiments of the invention. The capacitance for a parallel plate capacitor is defined as:

$$C = \frac{K\varepsilon_0 A}{t} \tag{11}$$

where C is capacitance in Farads, K is the dielectric constant of the material lying between the effective plates of the capacitor, A is the area of the smallest one of the effective plates of the capacitor in square meters, t is the separation of the surfaces of the effective plates in meters, and $\varepsilon_0$ is the permittivity of air in Farads/meter. There are two primary mechanisms by which the capacitance C can be varied: 1) patient contact area A (i.e. the area of the smallest one of the effective plates of the capacitor in square centimeters); and 2) materials lying between the patient and the return electrode (i.e. which can affect both K the dielectric constant of the material lying between the effective plates of the capacitor and t, the separation of the surfaces of the effective plates in meters). By providing parameters to control the variability in materials positioned between the patient and the return electrode 10, the dielectric constant of the material lying between the effective plates of the capacitor, $\varepsilon_0$ the permittivity of air in Farads/meter, and t the separation of the surfaces of the effective plates in meters will all be constants. However, due to the manner in which return electrode will typically be utilized, the patient contact area A (i.e. the area of the smallest one of the effective plates of the capacitor in square centimeters) will be variable. As will be appreciated by those skilled in the art, the area of the smallest one of the effective plates of the capacitor is the equivalent of the contact area between the patient and the return electrode, with the exceptions for edge effects as mentioned above.

The characteristics of the return electrode, the characteristics of the individual patient being operated on, and the surface area of the patient being operated on in contact with the return electrode will determine the value of the capacitive impedance experienced by the electrosurgical generator. This value will vary from procedure to procedure. Further, during the same procedure, this value may vary due to the patient shifting or other changes. The inductive impedance allows a user to counteract the capacitive component of the impedance caused by the patient on electrosurgical return electrode 10. Counteracting the capacitive impedance is done only insofar as the amount of contact area continues to be safe with respect to current densities. The self-limiting aspect of the return electrode, including a portion of the capacitive limiting impedance, is maintained such that current densities are limited when the contact area is reduced below safe levels in the absence of the limiting impedance. The ability to counteract the capacitive impedance of the return electrode and patient while maintaining the self-limiting aspect of the return electrode is shown in greater detail with reference to FIG. 5B.

Figure 5B:
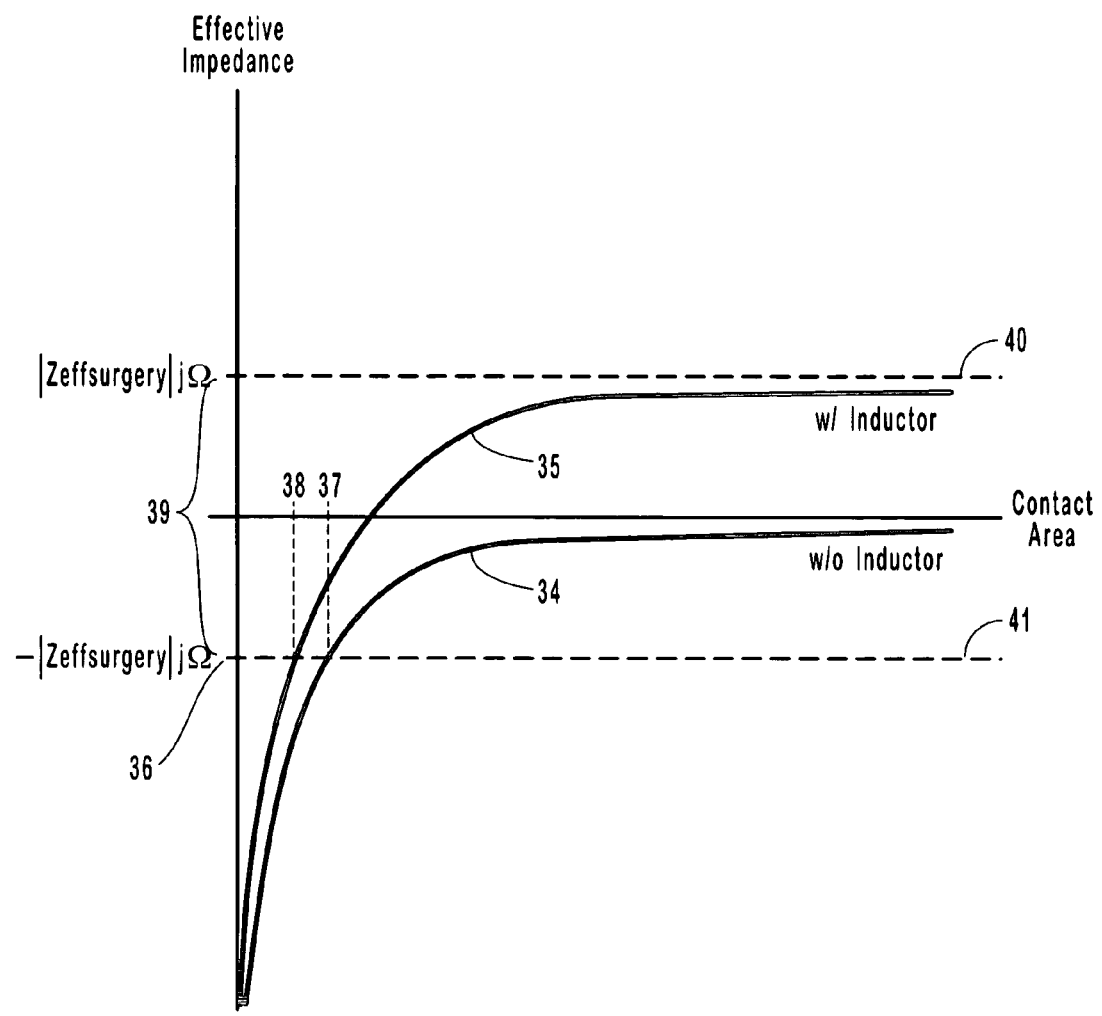
FIG. 5B is a chart illustrating in graphical form the relationship between the effective impedance of a return electrode, the contact area between a patient and a return electrode, and the effect of an inductor on the effective impedance.

There is shown in FIG. 5B a chart illustrating in graphical form the relationship between the effective impedance of a return electrode, the contact area between a patient and a return electrode, and the influence of an inductor on the effective impedance. However, before proceeding to a consideration of such chart, it should be noted that the chart is simplified so as to illustrate the principles underlying the invention and does not represent actual data that may vary substantially. The line graphs illustrate the effective impedance of a return electrode as a function of contact area between the patient and the return electrode.

Referring now to FIG. 5B, the effect of adding an inductor in series with the electrosurgical circuit described herein is demonstrated. FIG. 5B shows a line graph where the horizontal axis represents the contact area between the patient and return electrode 10, while the vertical axis represents the reactive impedance presented to the electrosurgical generator 12 (FIG. 1). Ordinarily, reactive impedances have a phase angle associated with them. In a net capacitive circuit, the phase angle causes the impedance to be expressed as a negative value whereas inductive circuits have positive values. However, electrosurgical generators have a threshold impedance at which they can operate, and that threshold is dependent on the magnitude of the impedance and not on the phase angle or sign. Thus, capacitive circuits and inductive circuits with the same impedance magnitude function equally efficiently.

The lower trace 34 represents the impedance seen by the electrosurgical generator 12 (FIG. 1) when no series inductor is coupled in the circuit. Much of this impedance is caused by the capacitive nature of return electrode 10 (FIG. 1) when used with a patient. The upper trace 35 represents the case when an inductor is coupled in series as described above in conjunction with the description of FIG. 3. By selecting an appropriate inductor, the overall impedance seen by electrosurgical generator 12 (FIG. 1) may be adjusted by counteracting the capacitive impedance caused by return electrode 10 (FIG. 1) and the patient acting as a parallel plate capacitor.

There exits a limiting impedance 36 that when seen by electrosurgical generator 12 (FIG. 1) will prevent electrosurgical generator 12 (FIG. 1) from providing the needed current to perform electrosurgical surgery. As described above, this limiting impedance 36 is designed to correspond to some specific quantity of area of a patient in contact with return electrode 10 (FIG. 1). It is therefore desirable that any modification to electrosurgical generator 12 (FIG. 1) or associated circuitry does not cause a significant variance in the contact area required for limiting impedance 36 to be seen by electrosurgical generator 12 (FIG. 1). Examining FIG. 5B, it is observed that the addition of the series inductor does not cause a significant change in the contact area needed to present limiting impedance 36 to electrosurgical generator 12 (FIG. 1). For example, when no inductor is provided (lower trace 34), the contact area required to present limiting impedance 36 to electrosurgical generator 12 (FIG. 1) is shown as contact area 37. With the addition of an inductor (upper trace 35), the contact area required to present limiting impedance 36 to electrosurgical generator 12 (FIG. 1) is shown as contact area 38. The sharp increase in the effective impedance in both lower trace 34 and upper trace 35 as the contact area decreases is caused by the return electrode design and the nature of capacitive and inductive loads. Because of this sharp increase, there is only a small change in the contact area required to present limiting impedance 36 to electrosurgical generator 12 (FIG. 1) resulting from the addition of series inductor 20 (FIG. 1) to the electrosurgical circuit (FIG. 1).

FIG. 5B further illustrates a graph showing a range 39 within which effective electrosurgery can be performed. A positive reactive impedance represents a net inductive impedance whereas a negative reactive impedance represents a net capacitive impedance. As noted above, some electrosurgical generators will operate effectively so long as the magnitude of the effective impedance seen by the electrosurgical generator is less than some value. These generators do not operate any less efficiently if the effective impedance is capacitive rather than inductive or inductive rather than capacitive. Thus the important parameter is the magnitude of the impedance and not necessarily the phase angle or sign of the impedance. This range is demonstrated in FIG. 5B by the upper limit 40 which represents a reactive impedance that is positive (net inductive) but equal in magnitude to a lower limit 41 that is a negative reactive (net capacitive) impedance. Effective electrosurgery may be performed so long as, among other factors, the impedance seen by electrosurgical generator 12 (FIG. 1) is less than the upper limit 40 and greater than the lower limit 41.

Figure 5C:
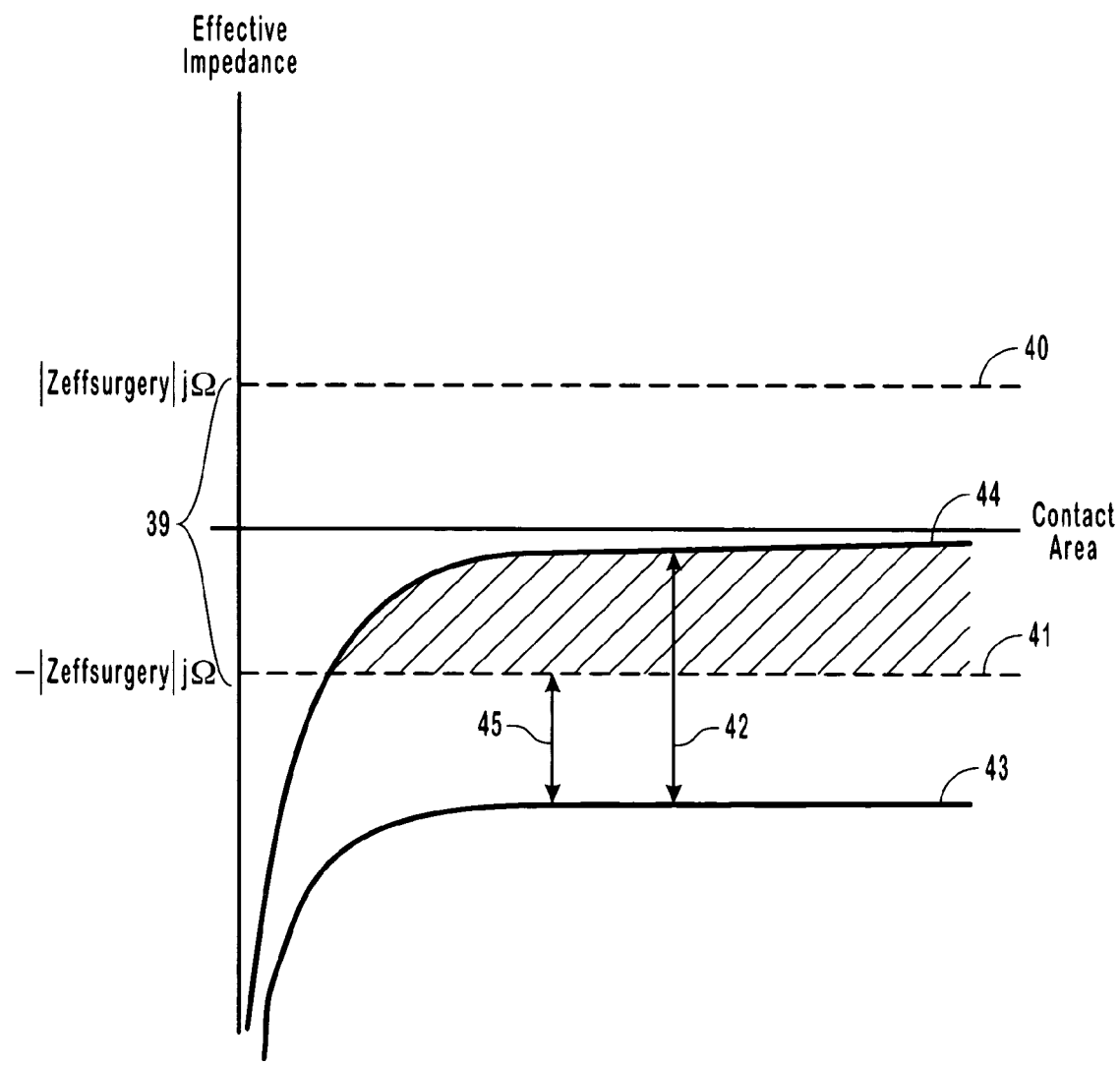
FIG. 5C is a chart illustrating in graphical form a desired range of reactive impedances within which effective electrosurgery may be performed and the relationship between the effective impedance of a return electrode, the contact area between a patient and a return electrode without the use of an inductor, in accordance with the present invention.
Figure 5D:
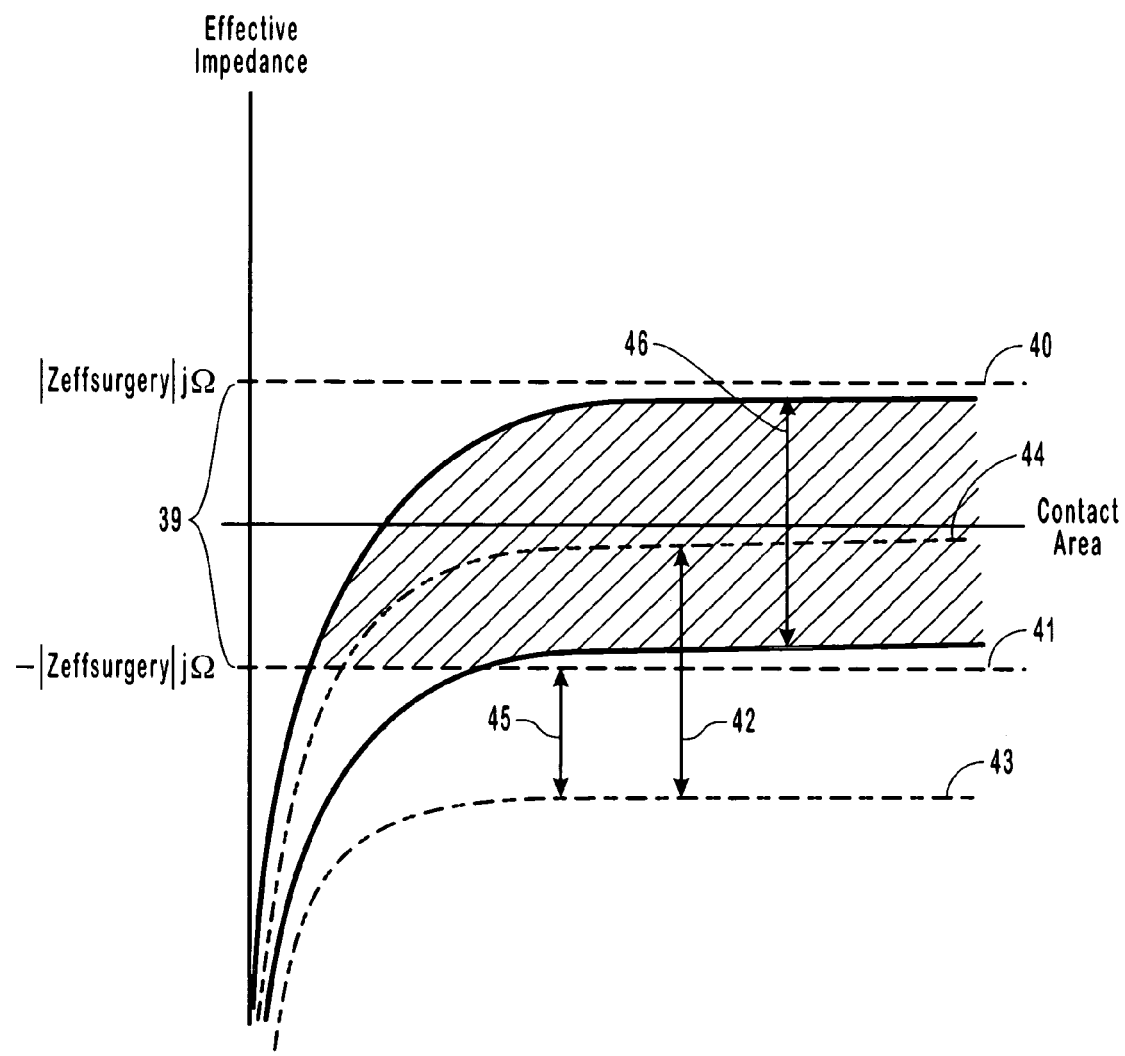
FIG. 5D is a chart illustrating in graphical form the relationship between the effective impedance of a return electrode, the contact area between a patient and a return electrode, and the effect of an inductor on the effective impedance.

FIG. 5C shows a range 42 of impedances that statistically most patients undergoing electrosurgery will present to electrosurgical generator 12 (FIG. 1). The range exists because of the different types of procedures, including TURPs and those involving neonatal patients, or because of differences in patient mass or body make-up. This range is shown where a series inductor is not used in the electrosurgical circuit. This range is represented by a lower impedance trace 43 and an upper impedance trace 44. Notably as seen in FIG. 5C, while some patients within this range 42 will fall into range 39 where effective electrosurgery may be performed (also graphically illustrated by the cross-hatched region shown in FIG. 5C), other patients such as those that fall within outer range 45, fall outside the range 39 where effective electrosurgery may be performed. The effect of adding a series inductor is graphically illustrated in FIG. 5D. By adding a series inductor to the electrosurgical circuit, range 42 may be shifted to an inductively compensated range 46 where inductively compensated range 46 falls within range 39 where effective electrosurgery may be performed. Thus, by adding a series inductor into the electrosurgical circuit, a significantly greater number of patients will fall within range 39 where effective electrosurgery may be performed (also graphically illustrated by comparing the cross-hatched region shown in FIG. 5C to the cross-hatched region shown in FIG. 5D). Therefore, in one embodiment of the invention effective surgery may be performed, using the same electrosurgical generator, on a range of patients that includes patients undergoing non-specialized surgeries as well as those undergoing surgeries such as TURPs or with neonatal patients.

Some of the ranges where electrosurgery may be performed are included below. The following examples should not be interpreted as limiting because the invention contemplates being used with a variety of different configurations with a number of different impedances in which electrosurgery may be performed. Further, as those skilled in the art readily understand and appreciate, a variety of mutually interdependent factors affect the ability to achieve an effective electrosurgical effect, such as the power level used, the overall effective impedance of the electrosurgical circuit, and other factors. Therefore, the following examples are given as representative examples only. For example, in applications using gel pads at relatively low power levels, effective surgery may be performed when the magnitude of the impedance seen by the electrosurgical generator is about 20 Ohms. In many applications involving moderately powered electrosurgical generators, electrosurgery may be performed in a range of impedances with magnitudes that are about 50 to 100 Ohms. Higher powered generators may perform electrosurgery in a range of impedances with magnitudes of about 200 to 400 Ohms.

Variable Inductor

Figure 6:
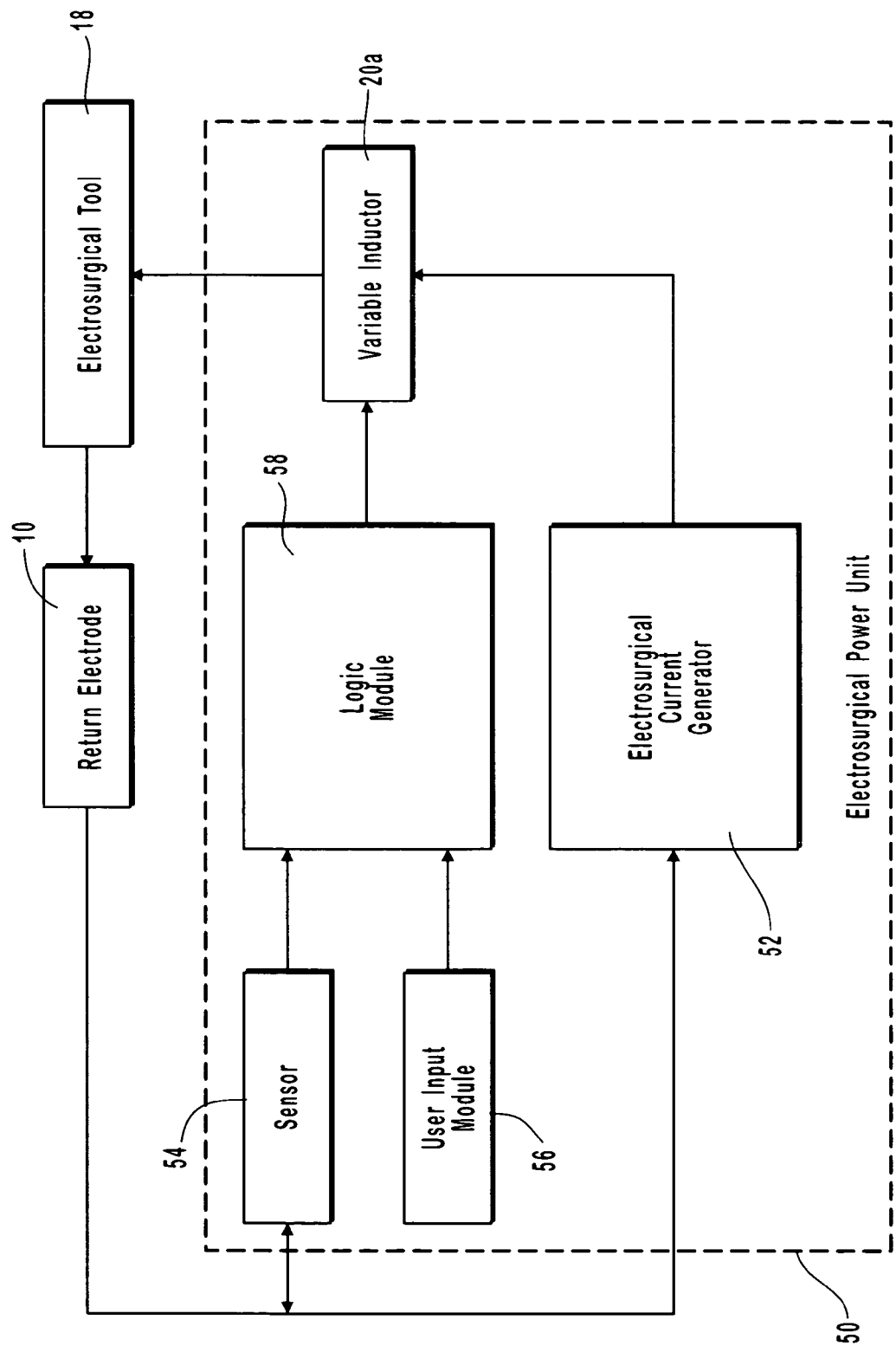
FIG. 6 is a block diagram illustrating an electrosurgical power unit having a tunable variable inductor.

With reference now to FIG. 6, there is shown a variable inductor 20a connected in series with a return electrode 10. There is also shown an electrosurgical power unit 50 having a logic module 58 adapted to tune variable inductor 20a to optimize the flow of the electrosurgical current by minimizing the capacitive reactance in the electrosurgical pathway. In the illustrated embodiment, electrosurgical power unit 50 includes an electrosurgical generator 52, a sensor 54, a user input module 56, and a logic module 58. Variable inductor 20a is positioned internal to electrosurgical power unit 50. There is also shown electrosurgical tool 18 and return electrode 10 connected in series with the variable inductor 20a. The apparatus of FIG. 6 is but one example of a mechanism for controlling the variable inductor. As will be appreciated by those skilled in the art, a variety of types and configurations of mechanisms can be utilized to control the variable inductor without departing from the scope and spirit of the present invention.

In another illustrative embodiment of the invention, the value of the variable inductor 20a can be set at the beginning of a surgery that takes into account characteristics of the patient or the particular surgery. Throughout the surgical procedure, the variable inductor is maintained at the value set at the beginning of the surgery. Thus, the entire electrosurgical circuit remains self-limiting should the area of contact between a patient and return electrode 10 be reduced sufficiently. While maintaining the self limiting nature of the circuit, specialized surgeries can be performed.

One example of such a surgery that has been herein described is surgery on neonatal patients. Neonatal patients have less surface area that may be in contact with return electrode 10. In some cases it may be difficult to contact a sufficient amount of surface area of return electrode 10 to perform effective electrosurgery. Examining FIG. 5B discussed previously herein, it may be observed that the amount of surface area required to perform effective electrosurgery may be reduced by the addition of a series inductor. FIG. 5B includes a threshold line 45 that represents the magnitude of impedance seen by an electrosurgical generator below which effective surgery can be performed. Less surface area is required to be below threshold 45 for performing electrosurgical surgery when an inductor is suitably configured at the beginning of the surgery than when no series inductor is in the electrosurgical circuit. While the amount of surface area may not be as significant in terms of current limiting when an adult patient is undergoing surgery, in neonatal patients that inherently have less surface area, it may make the difference of whether or not surgery may be performed. Nonetheless, while tuning or setting variable inductor 20a allows for surgery on neonatal patients to be performed, it does not eliminate for those surgeries the current limiting characteristics resulting from the design of the return electrode 10.

Variable inductor 20a is configured to provide different amounts of inductance in the electrosurgical pathway. This allows the amount of inductive reactance to be varied as the capacitive reactance varies. As discussed with reference to FIGS. 5A and 5B, the capacitive reactance varies as a function of the contact area and the materials between the patient and the return electrode 10. Due to the manner in which self-limiting return electrodes are typically used, the contact area and the amount of capacitive reactance in the electrosurgical pathway will often fluctuate. By utilizing variable inductor 20a, the amount of inductance can be changed corresponding with changes in the capacitive reactance to provide optimal levels of electrosurgical current flow. In the preferred embodiment, the amount of inductance that can be provided by the variable inductor is limited such that the capacitive reactance can only be minimized when the contact area between the patient and the return electrode is greater than the minimum contact area. This allows the variable inductor to counteract the capacitive reactance of the return electrode when the patient is in sufficient contact area with the electrosurgical electrode to perform safe and effective electrosurgery. However, when the contact area is less than the minimum contact area, the effective impedance of the pad is sufficient to limit the electrosurgical current to safe levels.

As will be appreciated by those skilled in the art, a variety of types and configurations of variable inductors can be utilized to provide varying amounts of inductance in the electrosurgical pathway. For example, in one embodiment, variable inductor 20 includes a plurality of inductors arranged in an inductor array with each inductor being configured to be utilized alone, or in combination, to provide varying amounts of inductance in the electrosurgical pathway, with each inductor providing a set amount of inductance. The inductors of the array may be added to or removed from the circuit by user actuated mechanical switches, solid-state switches controlled by a digital or other control circuit, electromechanical relays, or any other suitable switching method or apparatus. In an alternative embodiment, the variable inductor includes an electromechanical inductor that is regulated by a control module to provide varying amounts of inductance. In yet another alternative embodiment, a solid-state inductor may be used where the solid-state inductor is tunable by digital or other controls. In yet another embodiment, wave shaping power generators may be used to generate a signal with an appropriate phase angle to cancel the phase angle created by capacitive reactances in the circuit.

Sensor 54 and logic module 58 are adapted to determine the amount of capacitive reactance in the electrosurgical pathway and tune the variable inductor to optimize the flow of the electrosurgical current by minimizing the capacitive reactance. Sensor 54 is configured to identify the properties of the electrosurgical current returning to the electrosurgical power unit 50 from return electrode 10. Sensor 54 then relays the information regarding the properties of the electrosurgical current to logic module 58. Logic module 58 utilizes the properties of the electrosurgical current to determine the amount of impedance in the electrosurgical pathway and calculate the amount of capacitive reactance in the electrosurgical pathway. Once the amount of impedance in the electrosurgical pathway is determined, logic module 58 tunes variable inductor 20a to provide a desired amount of inductive reactance to minimize the capacitive reactance in the electrosurgical pathway. A variety of types and configurations of sensors and logic modules can be utilized within the scope and spirit of the present invention. For example, in one embodiment, the sensor and the logic module are integrated in a microprocessor. In an alternative embodiment, the sensor and logic module comprise separate hardware circuitry.

User input module 56 is configured to allow a user to provide input to logic module 58 to control the amount of inductance provided by variable inductor 20a. The functionality, configuration, and purpose of user input module can be tailored to the needs of the user. For example, user input module 56 can include a button allowing the user to place electrosurgical power unit 50 in a condition preferred for specialized procedures such as neonatal surgeries or TURP procedures. When electrosurgical power unit 50 is in a condition preferred for specialize procedures, logic module 58 tunes variable inductor 20a to minimize the impedance to the extent required, or based on special properties of the electrosurgical apparatus employed, for those procedures.

Figure 7:
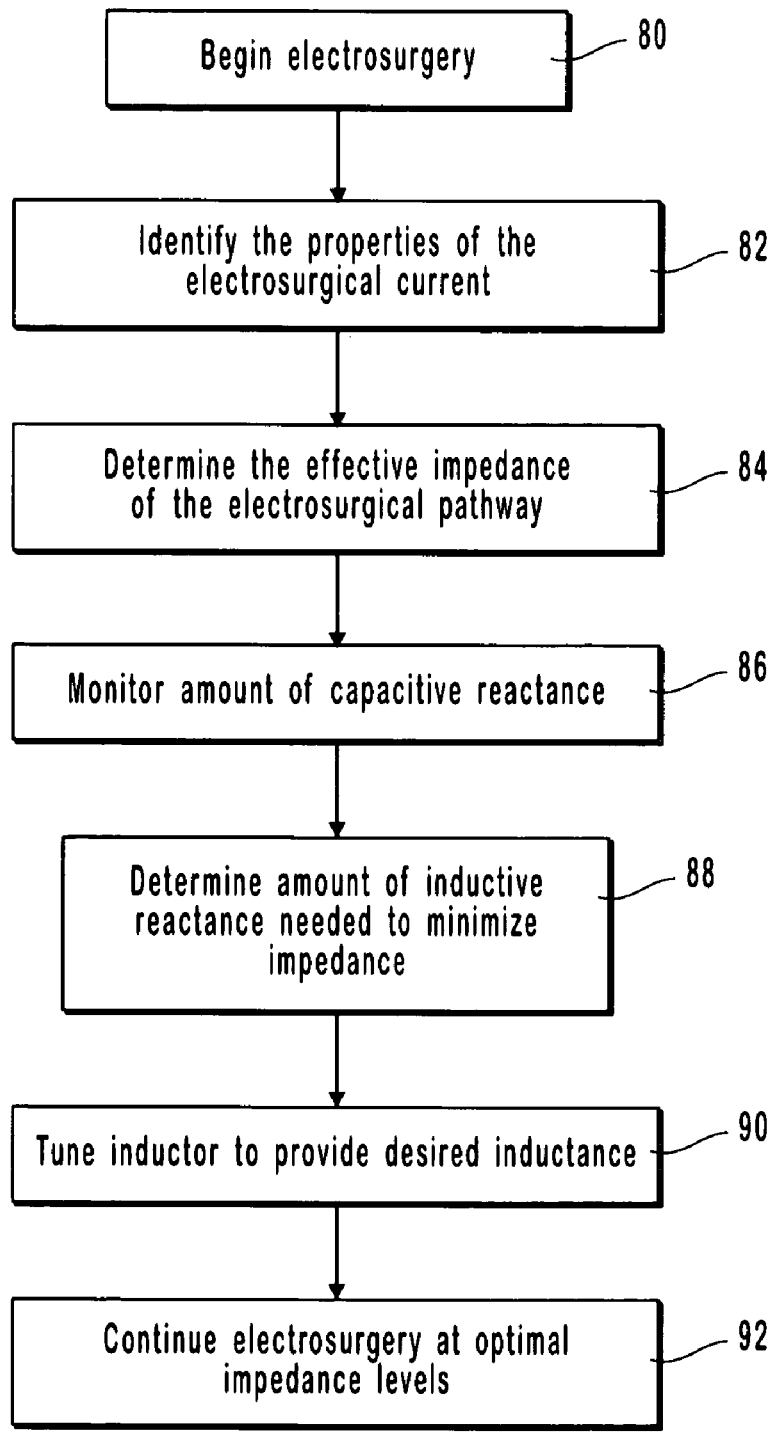
FIG. 7 is a flow diagram illustrating a method for utilizing a variable inductor to change the amount of inductance based on the amount of contact area between the patient and the electrosurgical return electrode.

With reference now to FIG. 7, there is shown a method for utilizing a variable inductor to provide an amount of impedance based on a patient contact area. According to the method, electrosurgery is started in step 80. Once electrosurgery is started, the properties of the electrosurgical current are identified in step 82. Based on the properties of the electrosurgical current, the effective impedance exhibited by the electrosurgical pathway is determined in step 82. Based on the effective impedance exhibited by the electrosurgical pathway, the amount of capacitive reactance of the return electrode is calculated in step 86. Using the amount of capacitive reactance of the return electrode, the amount of inductive reactance needed to minimize the impedance of the return electrode is determined in step 88. The variable inductor is then tuned to provide the amount of inductance necessary to realize the needed inductive reactance in step 90. Once the variable inductor is tuned to provide the desired amount of inductance, electrosurgery is continued at optimal impedance levels in step 92.

A variety of methods for identifying a capacitive reactance and tuning a variable inductor can be utilized without departing from the scope or spirit of the present invention. For example, an electrode of the size and type that is typically utilized during electrocardiogram procedures can be utilized with a separate monitoring current to determine the capacitive reactance of the return electrode before, during, or after the procedure. In another embodiment, the variable inductor can be continually adjusted during the course of a surgical procedure to provide an optimal amount of inductance as the patient contact area and capacitive reactance varies. In yet another embodiment, the voltage supplied by the electrosurgical generator can be compared to the current flowing through the circuit to determine the phase angle between the voltage and current such that the capacitive component of the impedance can be calculated.

While the present invention is described above primarily with reference to a series inductor for use with a capacitive electrosurgical return electrode, a series capacitor can be utilized with a self-limiting electrosurgical return electrode having an inductive component without departing from the scope and spirit of the present invention. In the embodiment, the series capacitor provides a level of capacitive reactance needed to counteract the inductive reactance of the electrosurgical return electrode. A variety of types and configurations of the series capacitors can be utilized without departing from the scope and spirit of the present invention.

Contact Quality Monitoring

Figure 8:
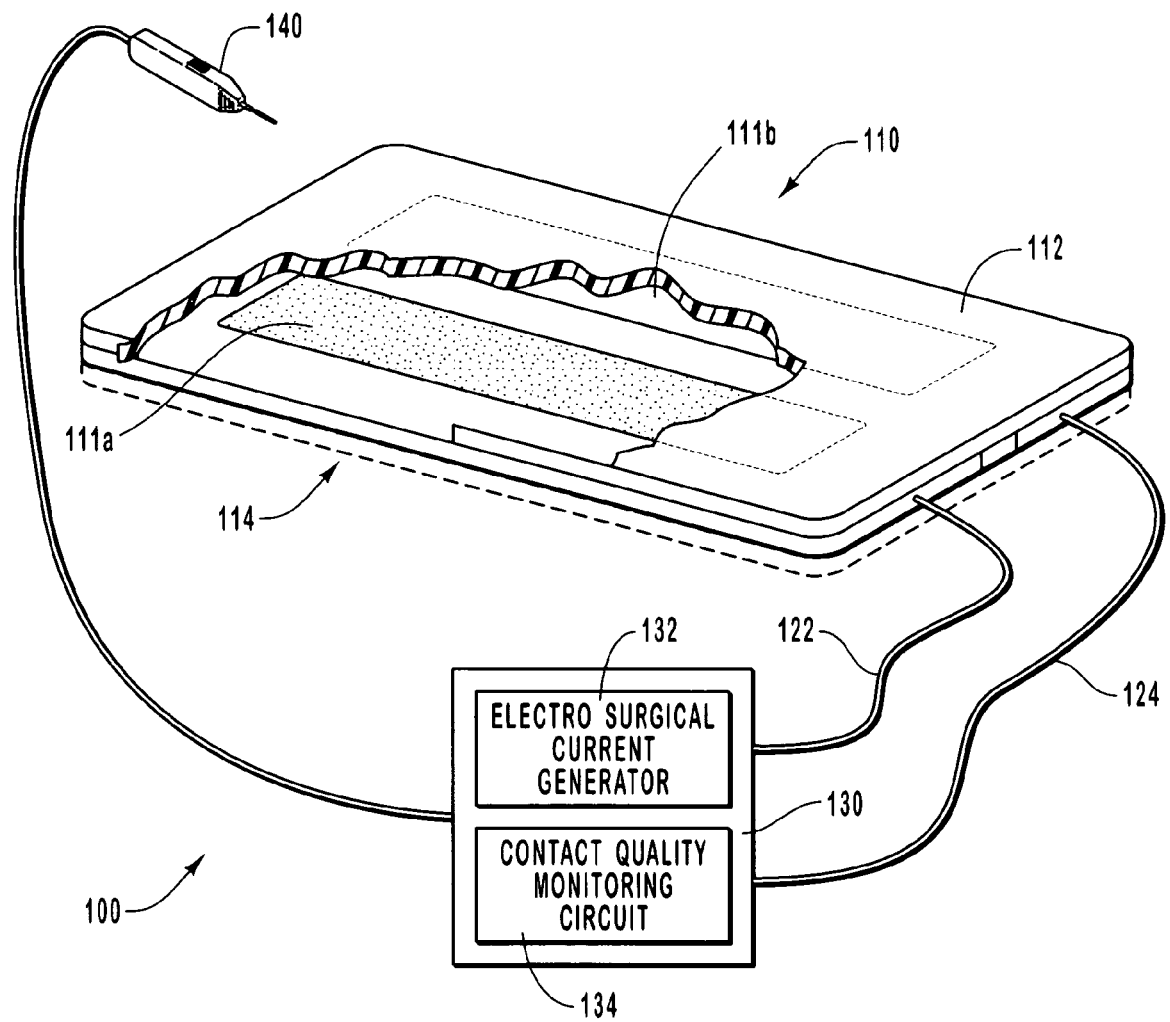
FIG. 8 is a perspective view of an electrosurgical return electrode for use with a contact quality monitoring apparatus having a semi-insulating member and conductor members according to the present invention.

With reference now to FIG. 8, there is shown an electrosurgical system 110 that utilizes one or more aspects of the present invention. As depicted, system 100 includes an electrosurgical return electrode 110 that communicates with an electrosurgical power unit 130 via members 122 and 124. The electrosurgical power unit 130 delivers electrosurgical signals or radio frequency (RF) energy to an electrosurgical tool or instrument 140 that can be used during a procedure to cut and/or coagulate tissue of a patient.

The electrosurgical power unit 130 also includes contact quality monitoring circuitry 134. In the illustrated embodiment, circuitry 134 creates a contact quality monitoring signal that is delivered to electrosurgical return electrode 110 utilizing member 124. In other configurations, the monitoring signal is deliverable along members 122 and/or 124. This monitoring signal can have a variety of different waveforms, frequencies, power levels, phase angle, or combinations thereof to allow circuitry 134 to measure, sense, and/or track the monitoring signal as it is delivered to and received from electrosurgical return electrode 110 along the monitoring path; the path extending from electrosurgical power unit 130, along member 124, through electrosurgical electrode 110 and a patient (not shown), and returning to electrosurgical power unit 130 along member 122. Differences in power, waveform, frequency, phase angle, or any other measurable characteristic or property of the monitoring signal can be measured, sensed, and/or tracked to identify whether a patient (not shown) is sufficiently in contact with electrosurgical electrode 110 to prevent patent burns. The signal generated by circuitry 134 may vary from the electrosurgical current generated by the electrosurgical current generator 132 such that by using appropriate filtering circuitry, the signal and current may be separated such that the monitoring signal characteristics may be measured.

In addition to the above, it will be appreciated by those skilled in the art that the monitoring signal and associated circuitry and path can be configured to provide a variety of information relating to the contact area between the patient and a return electrode of a variety of types and complexities. For example in one embodiment of the present invention, the monitoring circuitry can be configured to simply determine when the contact area falls below a predetermined threshold. In an alternative embodiment, the monitoring circuitry can be configured to determine the actual contact area and provide related information such as the amount of electrosurgical current and/or current densities. In yet another embodiment, the monitoring circuitry provides information needed to tune a variable inductor so as to counteract capacitive reactance in the electrosurgical circuit.

As shown, electrosurgical return electrode 110 electrically communicates with electrosurgical power unit 130 through members 122 and 124. Return electrode 110 is adapted to prevent patient burns by providing self-limiting capabilities and to function with circuitry 134 to determine whether the contact area between the patient and return electrode 110 is below a given threshold.

Return electrode 110, in the exemplary embodiment, includes a semi-insulating member 112 and a conductor member 114. In this configuration, semi-insulating member 112 is adapted to provide the self-limiting characteristics or capabilities of return electrode 110. Conductor member 114 is configured to permit contact quality monitoring circuitry to determine the contact area between return electrode 110, such as but not limited to semi-insulating member 112, and a patient resting thereon. In the illustrated embodiment, conductor member 114 has a split-plate configuration with a first conductor 111*a* and a second conductor 111*b*. Conductor member 114 need not be in direct physical contact with the patient. A patient can be in electrical connection with first conductor 111*a* and second conductor 111*b* without requiring the use of adhesives or gels. This also allows return electrode 110 to be re-used thereby eliminating the need and cost of disposable split-plate electrodes that are currently used.

In the illustrated embodiment, a monitoring signal is passed to conductor member 114, i.e. from first conductor 11*a* to second conductor 111*b*. Members 122 and 124 operate to relay the monitoring signal to and from contact quality monitoring circuit 134. At least one of members 122 and 124 also operates as the return path of the electrosurgical current. Where the contact area between the patient and return electrode 110 is very low, the total effective impedance perceptible by the monitoring signal or current will be very high and the magnitude of the monitoring signal or current will be minimized. Where the contact area between the patient and electrode 110 is above the minimum contact area, the total effective impedance will be lower allowing greater monitoring signal or current to flow. In other embodiments of the invention, the monitoring circuit may sense changes in phase angle, frequency or other characteristics to determine the contact area between the patient and return electrode 110.

By determining the amount of monitoring signal or current, the contact quality monitoring circuitry 134 determines whether the contact area between the patient and electrode 110, such as but not limited to semi-insulating member 112, is above a predetermined threshold (e.g. minimum contact area). Where the contact area is below the predetermined threshold the monitoring circuitry 134 activates an output device, such as but not limited to, an output device capable of delivering an audible signal, a visual signal, a tactile signal, or a combination thereof, to notify a physician or user that the contact area is insufficient to conduct effective surgery. As will be appreciated by those skilled in the art, the contact quality monitoring circuitry can be configured to determine the amount of contact area between a patient and a return electrode in a variety of manners utilizing an electrosurgical return electrode having one or a combination of a resistive component, a capacitive component, and/or an inductive component.

Return Electrode Configuration

With reference now to FIGS. 9–13 there is shown a variety of configurations of conducting members. According to one aspect of the present invention, the conducting members of FIGS. 9–13 are adapted to be utilized with a gel-pad or other return electrode positioned directly on the patient's skin for promoting uniform flow of current over the surface of the return electrode. In an alternative embodiment, conducting members of FIGS. 9–13 are adapted to be used with circuitry 134 (see FIG. 8) of electrosurgical power unit 130, in which the conducting member allows circuitry 134 to determine whether the total contact area between the patient and the return electrode is within a given range or above a threshold level below which the patient receives a burn. One benefit of the configuration of the conducting members of FIGS. 9–13 is that the configuration permits circuitry 134 to optionally determine the amount of contact area between the patient and the return electrode notwithstanding the total surface area of the semi-insulating member and the portion of semi-insulating member the patient is contacting. For the sake of simplicity, the conducting members will be described for use with contact quality monitoring circuitry where the patient acts as a variable resistive component of a circuit between the conducting member, however as will be appreciated by those skilled in the art a variety of types and configurations of circuitry can be utilized within the scope and spirit of the present invention to determine whether the contact area between the patient and the semi-insulating member is below a given threshold.

The configuration of the conducting members of FIGS. 9–13 is particularly well suited for use with the semi-insulating member 112 of FIG. 8. Semi-insulating member 112 is configured to have a sufficient surface area to permit a patient to contact various portions of semi-insulating member 112 while maintaining a minimum contact area. Traditional split-plate electrodes having two independent conductive layers positioned side-by-side are not configured to allow contact quality monitoring circuitry to determine the amount of contact area independent of the location of the patient on a return electrode. For example, traditional split-plate electrodes are unable to identify that the patient contact area is sufficient to conduct safe and effective electrosurgery where the patient is contacting only one side of the return electrode. The configurations of conductive members of FIGS. 9–13 allow contact quality monitoring circuitry 134 to determine the amount of contact area between the patient and a return electrode notwithstanding the total surface area of the electrode and the portion of the electrode the patient is contacting. While the conducting members of FIGS. 9–13 are particularly well adapted for use with the semi-insulating member 112 of FIG. 8, it will be understood that conducting members of FIGS. 9–13 can be utilized with contact quality monitoring circuitry independently of a semi-insulating member.

Figure 9:
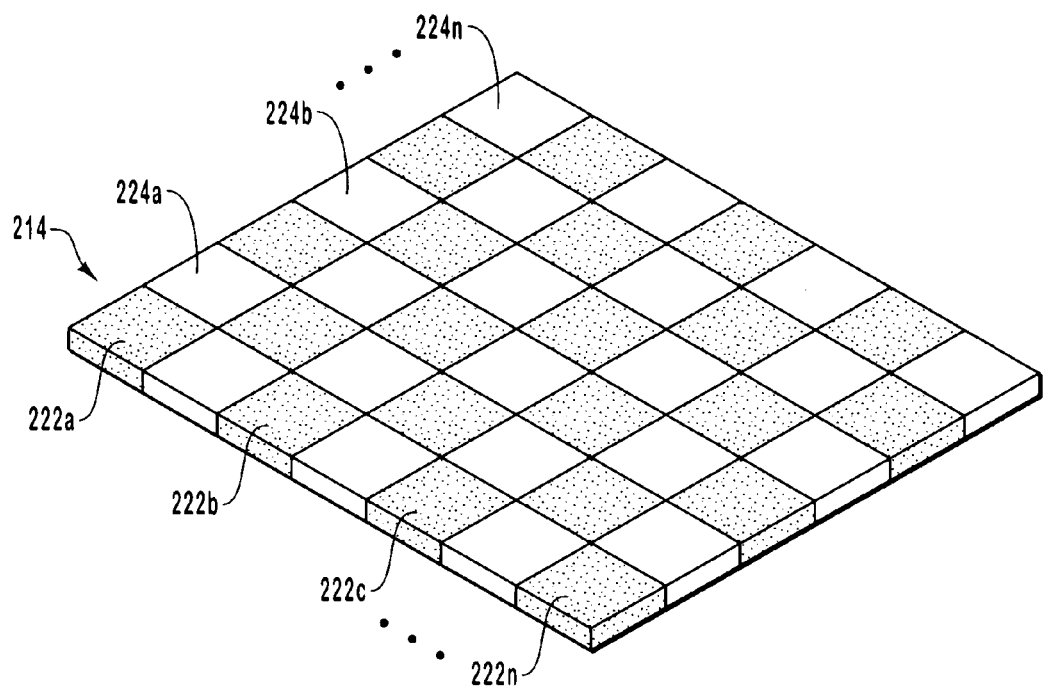
FIG. 9 illustrates a conductor member having a first and second conductor arranged in matrix of alternating segments.

With reference now to FIG. 9, there is shown a conductor member 214 in which segments of a first conductor 222 and a second conductor 224 are arranged in a matrix. First conductor 222 includes segments 222a–222n, while second conductor 224 includes segments 224a–224n. Segments 222a–222n are electrically isolated from segments 224a–224n such that a monitoring signal passes from first conductor 222 to second conductor 224 through the patient rather than directly from segments of first conductor 222 to the segments of second conductor 224.

Segments 222a–222n of first conductor 222 are electrically coupled to one another. Segments 224a–224n of second conductor 224 are also electrically coupled to one another. The contact quality control circuit is completed and current allowed to flow when segments 224a–224n and segments 222a–222n are in contact with the patient. The impedance created by placing the patient on the segments and electrically coupling the segments 224a–224n with segments 222a–222n through the patient is determined by the surface area of the segments in contact with the patient according to equation 4 above. Assuming that the patient is contacting the same amount of surface area of segments 222a–222n as segments 224a–224n and that the resistivity factor $\rho$ is known for the patient and the segments, or at least remains constant throughout the surgery, the impedance can be calculated or compared. The area designated by A is either ½ of the total area of the segments in contact with the patient or the area of either all of the segments 222a–222n or 224a–224n in contact with the patient. Ignoring the small differences that may occur at the edges of the patient contact area, the matrix configuration of segments 222a–222n and 224a–224n permits contact quality monitoring circuitry to determine whether the contact area between the patient and the return electrode is sufficient to avoid patient burns or allow effective surgery notwithstanding the total surface area of the semi-insulating member and the portion of semi-insulating member the patient is contacting.

While segments of first conductor 222 and second conductor 224 are depicted as having a checkerboard configuration, it will be understood that a variety of configurations of conductor member 214 are possible. For example, first conductor 222 and second conductor can be arranged in alternating stripes, triangles, ellipses, or any other configuration allowing the contact quality monitoring circuitry to determine the amount of contact area between the patient and the return electrode notwithstanding the total surface area of the return electrode and/or semi-insulating member and the portion of the return electrode and/or semi-insulating member the patient is contacting.

Figure 10:
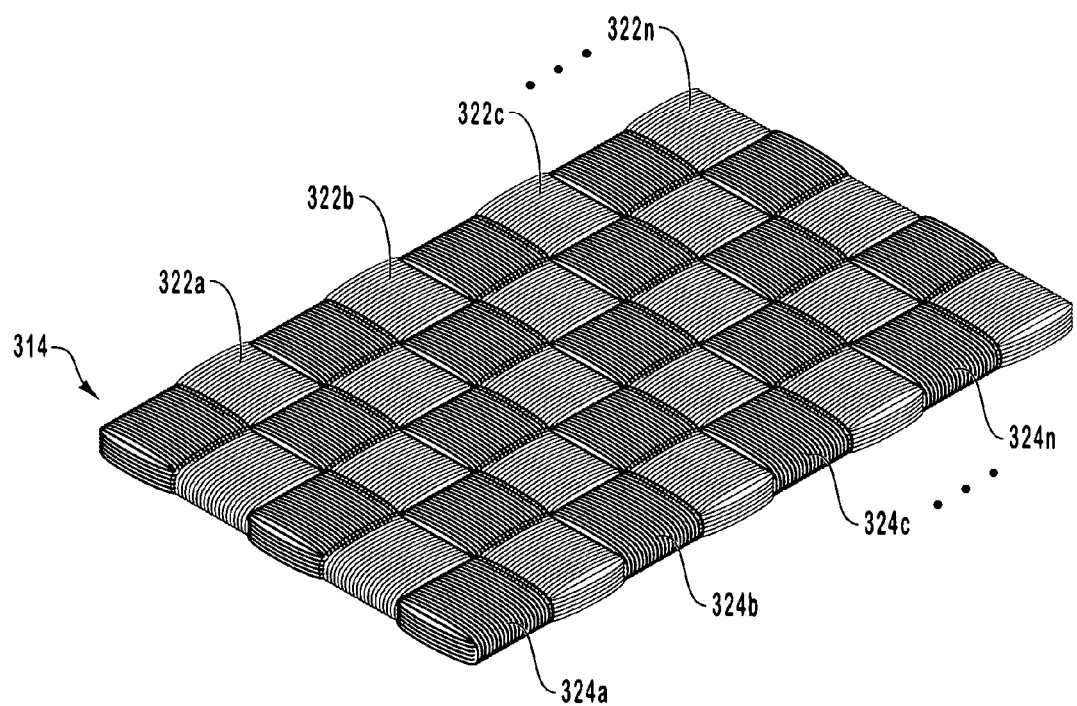
FIG. 10 illustrates a conductor member having a first conductor and a second conductor interwoven in a lattice structure.

FIG. 10 illustrates another alternative configuration of a conductor member 314. As illustrated, conductor member 314 includes a first conductor 322 and second conductor 324 that are interwoven in a lattice structure. The segments 322a–322n and 324a–324n are electrically coupled in parallel. Additionally, first and second conductors 322 and 324, respectively, are electrically isolated from one another. The interwoven lattice structure permits the segments to alternate while providing a configuration that allows for efficient and convenient manufacture of conductor 314.

Figure 11A:
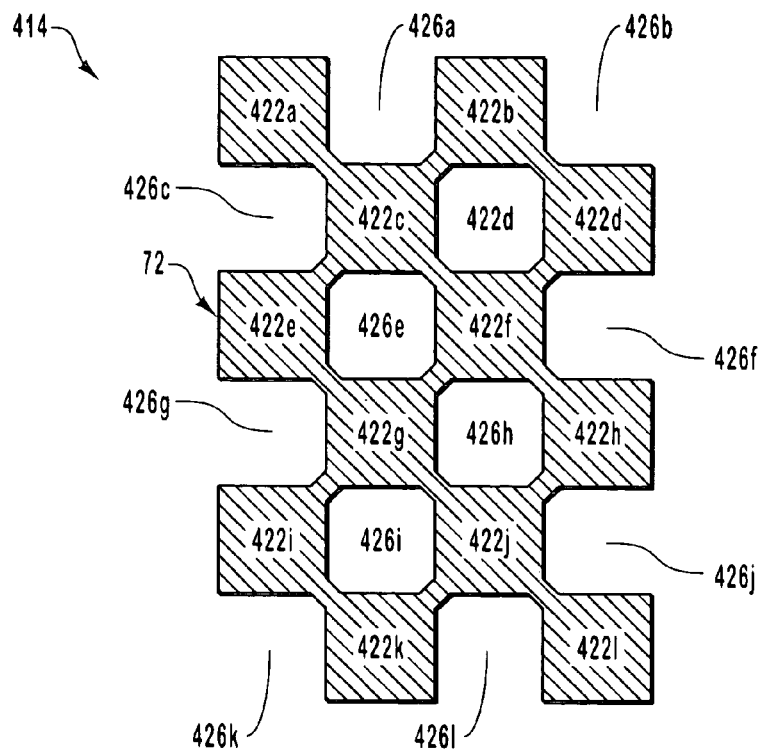
FIGS. 11A, B illustrate a first conductor and a second conductor that are configured to comprise a conductor member.
Figure 11B:
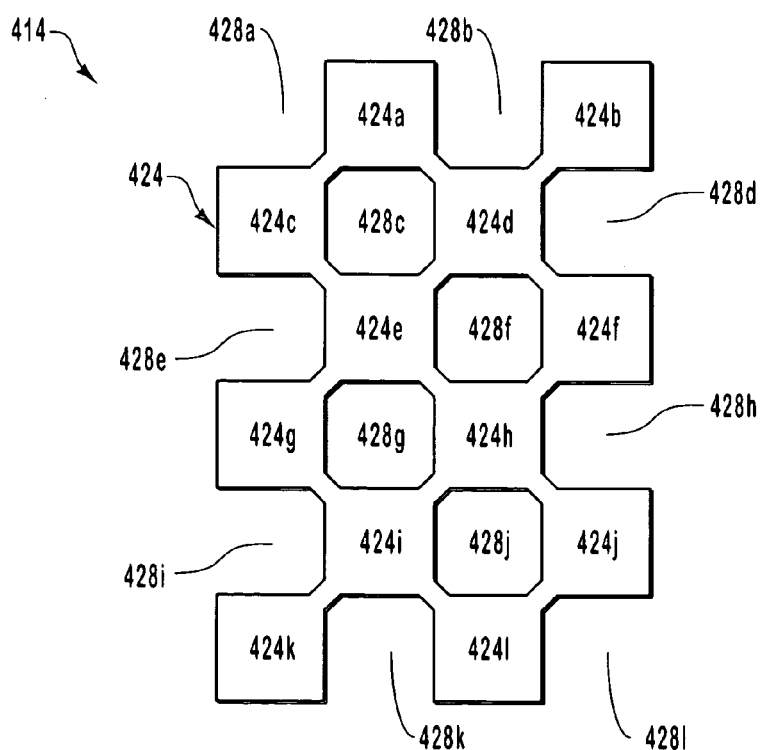

FIGS. 11A and 11B illustrate a first conductor 422 and second conductor 424 that are configured to form conductor member 414 having a split-plate type configuration. In the illustrated embodiment first conductor 422 includes a plurality of segments 422a–422n. Segments 422a–422n are defined by a plurality of voids 426a–426n. Similarly, second conductor 424 includes a plurality of segments 424a–424n and a plurality of voids 428a–428n. First conductor 422 and second conductor 424 can be manufactured by stamping a sheet of conductive material to create the segments and voids, or by any other acceptable manufacturing process. The segments and voids of first conductor 422 are configured to be out of alignment with the segments and voids of second conductor 424 such that when the first conductor 422 is placed over the second conductor 424 a matrix analogous to that shown in FIG. 9 is created.

As will be appreciated by those skilled in the art, the configuration of the conductor member is not limited to that shown in FIGS. 9–11. A variety of configurations of a conductor member can be utilized which allow the conductor member to be utilized with contact quality monitoring circuitry to determine the amount of contact area between the patient and the return electrode notwithstanding the total surface area of the semi-insulating member and the portion of the electrode and/or the semi-insulating member the patient is contacting. For example, a first conductor having a plurality of apertures formed therethrough can be placed in electrical isolation over a second continuous sheet conductor such that when a patient is positioned over a portion of the return electrode a monitoring signal can pass from the first conductor to the second conductor through the apertures.

Figure 12:
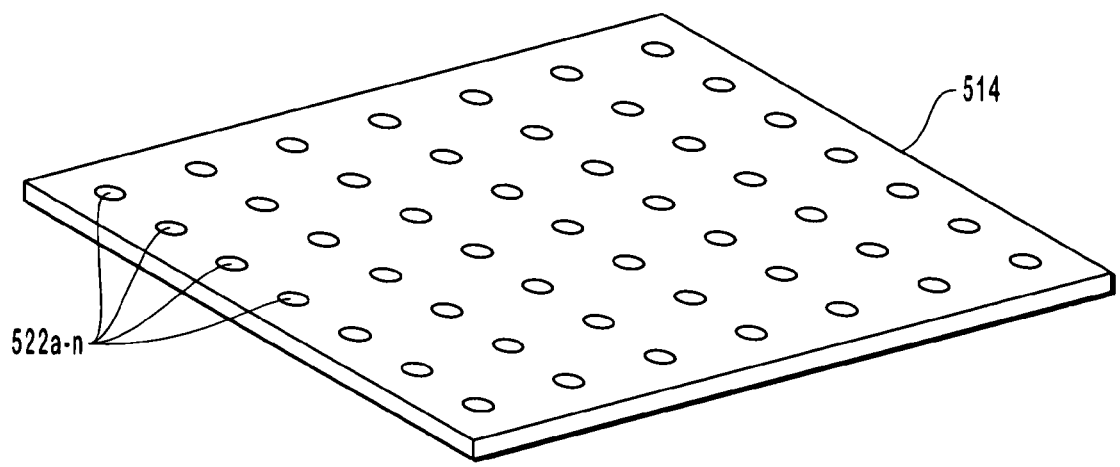
FIG. 12 is a perspective view illustrating a conductor member having a plurality of membrane switches.

With reference now to FIG. 12, there is shown a conductor member 514 having a plurality of membrane switches 522a–522n. The membrane switches electronically communicate with contact quality monitoring circuitry to receive a monitoring signal and return all or a portion of the signal to circuitry. In the illustrated embodiment, the plurality of membrane switches 522a–522n are adapted to permit circuitry to determine whether the contact area between the patient and return electrode is below a given threshold or threshold level below which the patient receives a burn. The configuration of membrane switches 522a–522n allows the contact area to be determined notwithstanding the total surface area of the return electrode and the portion of the return electrode the patient is touching. A variety of mechanisms can be utilized to determine the number of membrane switches depressed including, but not limited to, software, digital circuits, an impedance connected to the membrane switch, and the like.

As will be appreciated by those skilled in the art, while conductor member 514 is depicted as having a plurality of membrane switches 522a–522n, a variety of mechanisms can be used in the place of membrane switches without departing from the scope and spirit of the present invention. For example, an alternative electrical, mechanical, electromechanical, and/or any other mechanism can be used with conductor member 514 to indicate the amount contact area between the patient the return electrode such that a contact quality monitoring circuit can determine the amount of contact area between the patient and the return electrode notwithstanding the total surface area of the semi-insulating member and the portion of semi-insulating member the patient is contacting.

Figure 13:
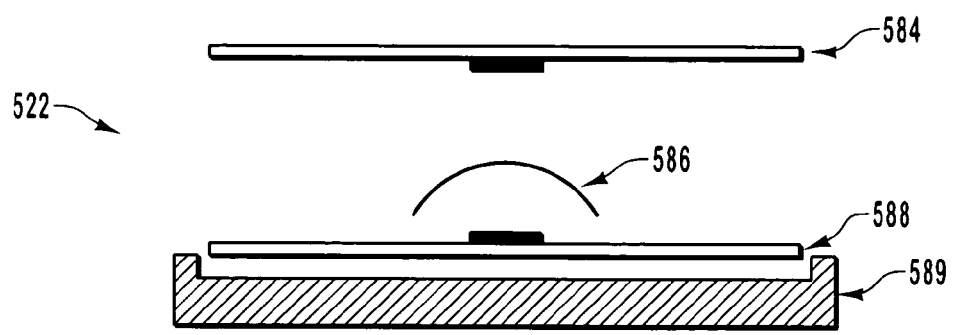
FIG. 13 is a cross-sectional exploded view illustrating the components of a membrane switch that can be utilized in connection with the conductor member of FIG. 12.

FIG. 13 illustrates exemplary components of a membrane switch 522 that can be utilized in connection with the conductor member 514 of FIG. 12. In the illustrated embodiment, membrane switch 522 includes a membrane layer 584, a tactile layer 586, a static layer 588, and a rigid layer 589. The membrane layer 584 includes a first conductor adapted to receive a monitoring signal or current from contact quality monitoring circuitry and is configured to be deformed in response to a force acting thereon. The tactile layer 586 includes a dome member and is configured to separate the membrane layer 584 from electrically coupling to static layer 588 until a force is applied to tactile layer 586 to deform tactile layer 586 so that tactile layer 586 comes into contact with static layer 588.

Static layer 588 comprises a second conductor configured to receive the monitoring signal or current from membrane layer 584 when membrane layer 584 and the tactile layer 586 are deformed. The static layer 588 is electrically coupled to contact quality monitoring circuitry to complete the monitoring path and allow circuitry 134 (FIG. 2) to determine the contact area between the patient and the return electrode.

The rigid layer 589 is configured to provide a substrate to prevent deformation of static layer 588 and maintain electrical coupling between membrane layer 584 and the static layer 588 when tactile layer 586 is deformed. In the illustrative embodiment, membrane layer 584 of each membrane switch is electrically coupled in parallel with the membrane layers of all the other membrane switches while the static layer 588 of each membrane switch is electrically coupled in parallel with the membrane layers of all other membrane switches.

As will be appreciated by those skilled in the art, a variety of types and configurations of membrane switches can be utilized without departing from the scope or spirit of the present invention. For example, in one embodiment a single static layer comprising a first conductor is positioned to be in contact with a plurality of membrane layers comprising a plurality of second conductors such that when a user is in contact with the surgical surface of the return electrode a monitoring signal can pass between the first conductor and each of the second conductors positioned in the portion of the return electrode in contact with the patient. The properties of the monitoring signal vary with the number of second elements passing a monitoring signal to the first element. The properties of the monitoring signal represent the amount of contact area between the patient and the electrosurgical surface.

Although the invention hereof has been described by way of preferred embodiments, it will be evident that adaptations and modifications may be employed without departing from the spirit and scope thereof.

The terms and expressions employed herein have been used as terms of description and not of limitation; and, thus, there is no intent of excluding equivalents, but, on the contrary, it is intended to cover any and all equivalents that may be employed without departing from the spirit and scope of the invention.

What is claimed is:

1. An electrosurgical apparatus comprising:
   (a) an electrosurgical return electrode having a bulk impedance sufficient to limit the density of an electrosurgical current to safe levels; and
   (b) an inductor coupled in series with the electrosurgical return electrode, wherein the inductor counteracts at least a portion of an effective impedance of the electrosurgical return electrode and a patient.

2. The electrosurgical apparatus of claim 1, wherein the inductor is selected from the group consisting of a solid state inductor, an electro-mechanical inductor, a fixed inductor, a variable inductor, solid state wave shaping circuitry or any combination thereof.

3. The electrosurgical apparatus of claim 1 wherein the inductor is selected such that the effective impedance of the electrosurgical return electrode, the patient, and the inductor falls within a range of impedances at which effective electrosurgery can be performed for a selected group of patients.

4. The electrosurgical apparatus of claim 1, wherein the effective impedance of the electrosurgical return electrode comprises a capacitive component.

5. The electrosurgical apparatus of claim 4, wherein the effective impedance of the electrosurgical return electrode further comprises a resistive component.

6. The electrosurgical apparatus of claim 4, wherein the effective impedance of the electrosurgical return electrode further comprises an inductive component.

7. The electrosurgical apparatus of claim 1, wherein the inductor optimizes the flow of the electrosurgical current by counteracting a capacitive component of the effective impedance of the electrosurgical return electrode.

8. The electrosurgical apparatus of claim 1, wherein the inductor controls the flow of electrical current by counteracting at least a portion of the effective impedance associated with the return electrode and the patient.

9. The electrosurgical apparatus of claim 8, wherein the return electrode is of a size that would normally be used on an adult sized patient and wherein the inductor counteracts the effective impedance associated with the return electrode and the patient such that electrosurgery on patients weighing less than 25 pounds can be performed effectively and safely.

10. The electrosurgical apparatus of claim 8, wherein the inductor counteracts at least a portion of the effective impedance associated with the return electrode and the patient such that the electrosurgical return electrode can be utilized for neonatal applications.

11. The electrosurgical apparatus of claim 8, wherein the inductor counteracts at least a portion of the effective impedance associated with the return electrode and the patients such that the electrosurgical return electrode can be utilized for pediatric applications.

12. The electrosurgical apparatus of claim 8, wherein the inductor counteracts at least a portion of the effective impedance associated with the return electrode and the patient such that the electrosurgical return electrode can be utilized for trans-urethral resection of the prostate applications.

13. The electrosurgical apparatus of claim 1, wherein an inductive reactance provided by the inductor counteract a portion of a capacitive reactance wherein the portion of the capacitive reactance is not needed to limit the density of the electrosurgical current to safe levels.

14. The electrosurgical apparatus of claim 13, wherein the portion of the capacitive reactance is not more than the capacitance of the effective impedance when the contact area between the patient and the return electrode is sufficient to limit the current density to safe levels without the bulk impedance.

15. An electrosurgical apparatus for use in electrosurgery wherein an electrosurgical current is utilized to cut and coagulate tissue, configured to limit the density of the electrosurgical current to safe levels so as to prevent unwanted patient burn, the electrosurgical apparatus comprising:

(a) an electrosurgical return electrode having a bulk impedance sufficient to limit the density of an electrosurgical current to safe levels, wherein the bulk impedance comprises a capacitive component; and (b) an inductor coupled in series with the electrosurgical return electrode, the inductor being configured to increase the flow of the electrosurgical current by counteracting at least a portion of the capacitive component of the effective impedance of the electrosurgical return electrode and a patient.

16. The electrosurgical apparatus of claim 15, wherein the inductor comprises a plurality of inductors.

17. The electrosurgical apparatus of claim 16, wherein the plurality of inductors are adapted to provide variable amounts of inductance.

18. The electrosurgical apparatus of claim 15, wherein the inductor comprises a variable inductor.

19. The electrosurgical apparatus of claim 18, wherein the variable inductor is tunable.

20. The electrosurgical apparatus of claim 19, wherein the variable inductor is tunable such that that the overall effective impedance is optimized for electrosurgery when the contact area between the electrosurgical return electrode and the patient is greater than the minimum contact area needed to prevent unwanted burns.

21. The electrosurgical apparatus of claim 19, wherein the variable inductor is tunable such that the overall effective impedance is optimized for electrosurgery when the contact area is sufficient to limit the electrosurgical current density to safe levels.

22. The electrosurgical apparatus of claim 18, further comprising a logic module to tune the impedance level of the variable inductor.

23. The electrosurgical apparatus of claim 18, further comprising a sensor adapted to sense the properties of the electrosurgical current such that the capacitive component of the electrosurgical effective impedance can be determined.

24. The electrosurgical apparatus of claim 15, wherein the return electrode is of a size that would normally be used on an adult sized patient and wherein the inductor counteracts the effective impedance associated with the return electrode and the patient such that electrosurgery on pediatric patients can be performed effectively and safely.

25. The electrosurgical apparatus of claim 15, wherein the inductor counteracts at least a portion of the effective impedance associated with the return electrode and the patient such that the electrosurgical return electrode can be utilized for pediatric applications.

26. An electrosurgical apparatus for use in electrosurgery wherein an electrosurgical current is utilized to cut and coagulate tissue, and to limit the density of the electrosurgical current to safe levels so as to prevent unwanted patient burn, the electrosurgical apparatus comprising:

(a) an electrosurgical return electrode having an bulk impedance sufficient to limit the density of an electrosurgical current to safe levels, wherein the electrosurgical return electrode has an effective impedance resulting from the properties of the bulk impedance and the contact area between the patient and the return electrode, the effective impedance having a capacitive component;

(b) a variable inductor coupled in series with the electrosurgical return electrode, the variable inductor being configured to increase the flow of the electrosurgical current by counteracting the capacitive component of the effective impedance of the electrosurgical return electrode when the amount of contact area between the patient and the electrosurgical return electrode is sufficient to conduct electrosurgery; and (c) circuitry adapted to identify the amount of capacitive reactance in an electrosurgical pathway including the electrosurgical generator and the variable inductor and tune the variable inductor to optimize the flow of the electrosurgical current by minimizing the capacitive reactance in the electrosurgical pathway.

27. The electrosurgical apparatus of claim 26, wherein the circuitry identifies the amount of capacitive reactance while electrosurgery is being performed.

28. The electrosurgical apparatus of claim 27, wherein the circuitry is adapted to tune the variable inductor while electrosurgery is being performed.

29. The electrosurgical apparatus of claim 26, wherein separate monitoring circuitry is utilized to identify the amount of capacitive reactance in the electrosurgical circuit.

30. The electrosurgical apparatus of claim 26, wherein the inductor is positioned in an electrosurgical tool.

31. The electrosurgical apparatus of claim 26, wherein the inductor is positioned in an electrosurgical generator.

32. The electrosurgical apparatus of claim 26, wherein the inductor is positioned in an electrosurgical generator.

33. The electrosurgical apparatus of claim 26, wherein the inductor is tunable such that the capacitive reactance is counteracted when the contact area between the patient and the electrosurgical electrode is sufficient to limit the electrosurgical current to safe levels.

34. The electrosurgical apparatus of claim 26, wherein the inductor is configured to maintain the impedance in the electrosurgical pathway above a level below which would result in unsafe electrosurgical current densities when the contact area between the patient and the electrosurgical electrode is insufficient to limit the electrosurgical current densities to safe levels without the bulk impedance.

35. The electrosurgical apparatus of claim 26, wherein the return electrode is of a size that would normally be used on an adult sized patient and wherein the inductor counteracts the effective impedance associated with the return electrode and the patient such that electrosurgery on pediatric patients can be performed effectively and safely.

36. The electrosurgical apparatus of claim 26, wherein the inductor counteracts at least a portion of the effective impedance associated with the return electrode and the patient such that the electrosurgical return electrode can be utilized for pediatric applications.

37. An electrosurgical apparatus for use in electrosurgery wherein an electrosurgical current is utilized to cut and coagulate tissue and to limit the density of the electrosurgical current to safe levels so as to prevent unwanted patient burn, the electrosurgical apparatus comprising:

(a) an electrosurgical return electrode adapted to contact a patient wherein the combination of the return electrode and the patient in contact with the return electrode comprises a capacitive reactance sufficient to limit the density of an electrosurgical current to safe levels, when the electrode is at least partially in contact with a patient;

(b) an inductor coupled in series with said electrode, the inductor being configured to increase the flow of the electrosurgical current by utilizing the phase angle and magnitude of the inductance to reduce the capacitive reactance of the electrode.

38. The electrosurgical apparatus of claim 37, wherein the properties of the inductor are selected based on the capacitive reactance of the electrode when a patient is in sufficient contact with the electrosurgical return electrode to limit the density of the electrosurgical current to safe levels.

39. The electrosurgical apparatus of claim 37, wherein said electrosurgical return electrode comprises electrically conducting material having an effective bulk impedance equal to or greater than about 4,000 Ω • cm.

40. The electrosurgical apparatus of claim 37, wherein said electrosurgical return electrode comprises an electrically conducting material having an effective bulk impedance equal to or greater than about 10,000 Ω • cm.

41. The electrosurgical apparatus of claim 37, wherein the capacitive reactance is sufficient to limit the electrosurgical current density to less than 100 milliamperes per centimeter.

42. The electrosurgical apparatus of claim 37, wherein the return electrode is of a size that would normally be used on an adult sized patient and wherein the inductor counteracts the effective impedance associated with the return electrode and the patient such that electrosurgery on pediatric patients can be performed effectively and safely.

43. The electrosurgical apparatus of claim 37, wherein the inductor counteracts at least a portion of the effective impedance associated with the return electrode and the patient such that the electrosurgical return electrode can be utilized for pediatric applications.

44. An electrosurgical return electrode adapted to prevent unwanted patient burns comprising:

a semi-insulating element having a bulk impedance sufficient to prevent a patient burn when a contact area between a patient and the semi-insulating element is below a given threshold;

an electrically conductive member coupled to the semi-insulating element, the conductive member cooperating with circuitry that identifies the area of contact between the patient and the semi-insulating element and if the area of contact is below a given threshold; and an inductor coupled in series with the bulk impedance wherein the inductor is configured to counteract at least a portion of an effective impedance caused when the patient is in limited contact with the electrosurgical return electrode.

45. The return electrode of claim 44, wherein the electrically conductive member comprises a split plate.

46. An electrosurgical return electrode adapted to prevent unwanted patient burns comprising:

a semi-insulating element having a bulk impedance sufficient to prevent a patient burn when a contact area between a patient and the semi-insulating element is below a given threshold;

an electrically conductive member coupled to the semi-insulating element, the conductive member cooperating with circuitry that identifies the area of contact between the patient and the semi-insulating element and if the area of contact is below a given threshold; and an inductor coupled in series with the bulk impedance wherein the inductor is configured to counteract at least a portion of an effective impedance caused when the patient is in limited contact with the electrosurgical return electrode.

47. The return electrode of claim 46, wherein the electrically conductive member comprises a split plate.

48. The return electrode of claim 47, wherein the split plate is configured such that the area of contact between the patient and the semi-insulating element can be measured notwithstanding the total surface area of the semi-insulating element and the portion of semi-insulating element the patient is contacting.

49. The return electrode of claim 48, wherein the split plate comprises a split plate member having a first conductor and a second conductor interwoven in a lattice structure.

50. The return electrode of claim 49, wherein the circuitry measures the impedance between the first conductor and the second conductor.

51. The electrosurgical return electrode of claim 44, wherein the return electrode is of a size that would normally be used on an adult sized patient and wherein the inductor counteracts the effective impedance associated with the return electrode and the patient such that electrosurgery on pediatric patients can be performed effectively and safely.

52. The electrosurgical return electrode of claim 44, wherein the inductor counteracts at least a portion of the effective impedance associated with the return electrode and the patient such that the electrosurgical return electrode can be utilized for pediatric applications.

53. A return electrode having a surface adapted to be positioned directly on a patient, the return electrode comprising:
a first conductor;
a second conductor interwoven with the first conductor to create a lattice structure where the lattice structures promotes uniform flow of current over the surface of the return electrode, wherein the first and second conductors comprise a bulk impedance sufficient to prevent a patient burn when a contact area between a patient and the first and second conductors is below a given threshold; and
an inductor coupled in series with the bulk impedance wherein the inductor is configured to counteract at least a portion of an effective impedance caused when the patient is in contact with the first and second conductors.

54. The return electrode of claim 53, wherein the inductor is selected from the group consisting of a solid state inductor, an electro-mechanical inductor, a fixed inductor, a variable inductor, solid state wave shaping circuitry or any combination thereof.

55. The return electrode of claim 53, wherein the inductor is selected such that the effective impedance falls within a range of impedances at which effective electrosurgery can be performed for a selected group of patients.

56. The return electrode of claim 53, wherein the effective impedance comprises a capacitive component.

57. The return electrode of claim 56, wherein the effective impedance further comprises a resistive component.

58. The return electrode of claim 56, wherein the effective impedance further comprises an inductive component.

59. The return electrode of claim 53, wherein the inductor counteracts a capacitive component of the effective impedance of the electrosurgical return electrode.

60. The return electrode of claim 53, wherein the return electrode is of a size that would normally be used on an adult sized patient and wherein the inductor counteracts the effective impedance caused by the patient being in contact with the first and second conductors such that electrosurgery on pediatric patients can be performed effectively and safely.

61. The return electrode of claim 53, wherein the inductor counteracts at least a portion of the effective impedance caused by the patient being in contact with the first and second conductors such that the electrosurgical return electrode can be utilized for pediatric applications.

62. An electrosurgical apparatus comprising:
(a) an electrosurgical return electrode having a bulk impedance sufficient to limit the density of an electrosurgical current to safe levels; and
(b) a reactance coupled in series with the electrosurgical return electrode, the reactance being configured to increase the flow of the electrosurgical current by counteracting a portion of an effective impedance caused when a patient is in contact with the electrosurgical return electrode.

63. The electrosurgical apparatus of claim 62, wherein the effective impedance includes an inductive component.

64. The electrosurgical apparatus of claim 63, wherein the reactance is a capacitor coupled in series with the electrosurgical return electrode configured to counteract at least a portion of the inductive component.

65. The electrosurgical apparatus of claim 64, wherein the capacitor is configured to not reduce the combination of the effective impedance and the reactance to a level that would allow unsafe electrosurgical current densities when the contact area between the patient and the electrosurgical return electrode is insufficient to limit the electrosurgical current densities to safe levels without the bulk impedance.

66. The electrosurgical apparatus of claim 63, further comprising monitoring circuitry to identify the inductive component of the effective impedance.

67. The electrosurgical apparatus of claim 62, wherein the reactance is selected such that the combination of the effective impedance and the reactance falls within a range of impedance at which effective electrosurgery can be performed for a selected group of patients.

68. The electrosurgical apparatus of claim 62, wherein the return electrode is of a size that would normally be used on an adult sized patient and wherein the inductor counteracts the effective impedance associated with the return electrode and the patient such that electrosurgery on pediatric patients can be performed effectively and safely.

69. The electrosurgical apparatus of claim 62, wherein the inductor counteracts at least a portion of the effective impedance associated with the return electrode and the patient such that the electrosurgical return electrode can be utilized for pediatric applications.

* * * * *

UNITED STATES PATENT AND TRADEMARK OFFICE
CERTIFICATE OF CORRECTION

| | | |
|---|---|---|
| PATENT NO. | : 7,169,145 B2 | Page 1 of 3 |
| APPLICATION NO. | : 10/719333 | |
| DATED | : January 30, 2007 | |
| INVENTOR(S) | : Isaacson et al. | |

It is certified that error appears in the above-identified patent and that said Letters Patent is hereby corrected as shown below:

Drawings
Sheet 12, replace FIG 11A with the figure depicted herein below, wherein "422d" has been changed to --426d-- and "72" has been changed to --422--

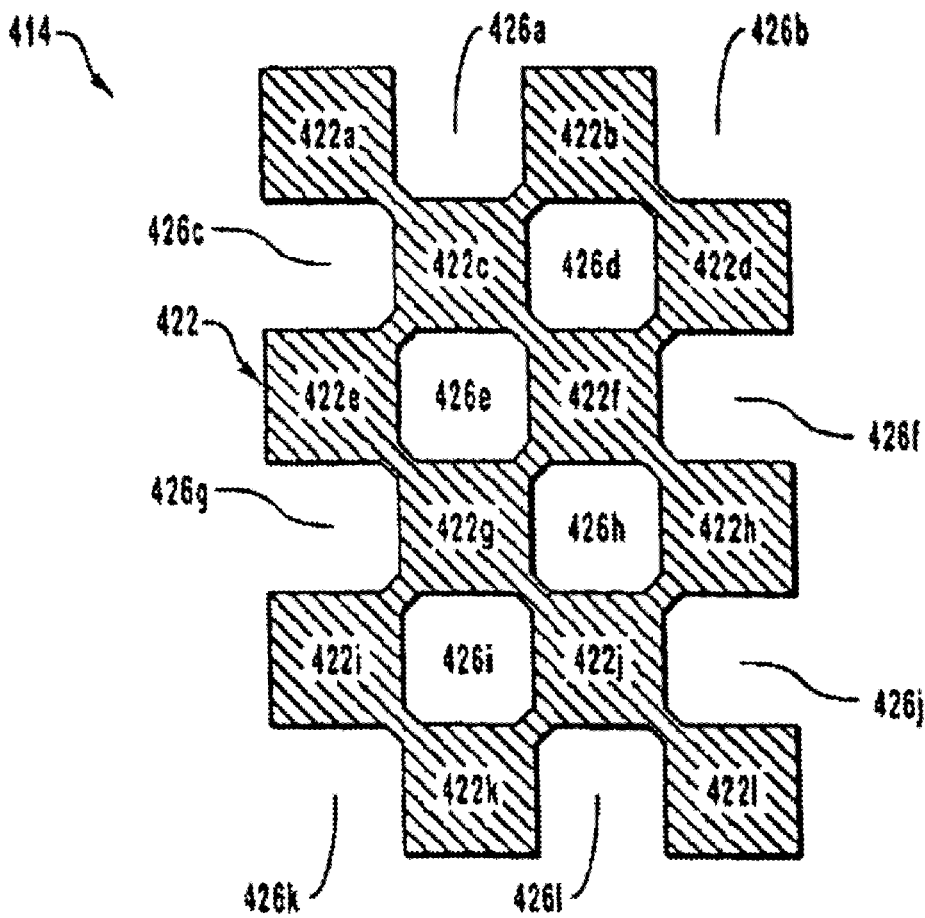

FIG. 11A

UNITED STATES PATENT AND TRADEMARK OFFICE
CERTIFICATE OF CORRECTION

PATENT NO.       : 7,169,145 B2
APPLICATION NO.  : 10/719333
DATED            : January 30, 2007
INVENTOR(S)      : Isaacson et al.

It is certified that error appears in the above-identified patent and that said Letters Patent is hereby corrected as shown below:

Column 1
Line 67, after "burns", insert --,--

Column 7
Line 18, after "including", insert --,--

Column 11
Line 53, after "Thus", insert --,--

Column 12
Line 57, change "-j" to --j--

Column 16
Line 17, after "K", insert --,--
Line 19, after "capacitor", insert --,--

Column 17
Line 27, change "exits" to --exists--

Column 18
Line 17, after "Notably", insert --,--

Column 19
Line 34, change "45" to --40 and 41--
Line 37, change "45" to --41--

Column 21
Line 8, change "82" to --84--
Line 11, change "calculated" to --monitored--
Line 51, change "110" to --100--

Column 23
Line 11, change "such as but not limited to" to --such as, but not limited to,--
Line 15, change "such as but" to --such as, but--

UNITED STATES PATENT AND TRADEMARK OFFICE
CERTIFICATE OF CORRECTION

PATENT NO. : 7,169,145 B2
APPLICATION NO. : 10/719333
DATED : January 30, 2007
INVENTOR(S) : Isaacson et al.

It is certified that error appears in the above-identified patent and that said Letters Patent is hereby corrected as shown below:

Column 26
Line 15, after "applied to", change "tactile layer 586" to --membrane layer 584--
Line 16, after "so that", change "tactile layer 586" to --membrane layer 584--
Line 23, change "FIG. 2" to --FIG. 8--

Column 27
Line 8, after "claim 1", insert --,--

Column 29
Line 26, change "an electrosurgical generator" to --cabling--

Column 30
Lines 47-64, replace claims 46 and 47 with the following claims:
--    46.   The return electrode of claim 44, wherein the electrically conductive member includes a plurality of membrane switches.
       47.   The return electrode of claim 44, further comprising monitoring circuitry to identify a capacitive reactance portion of the effective impedance--
Line 63, change "46" to --44--
Line 64, change "46" to --44--

Signed and Sealed this

Eleventh Day of March, 2008

JON W. DUDAS
*Director of the United States Patent and Trademark Office*